(12) United States Patent
Schoonover et al.

(10) Patent No.: US 10,052,452 B2
(45) Date of Patent: Aug. 21, 2018

(54) DREAM ENHANCEMENT APPARATUS AND METHOD

(71) Applicants: Daniel Carleton Schoonover, Costa Mesa, CA (US); Andrew Holland Smiley, San Diego, CA (US)

(72) Inventors: Daniel Carleton Schoonover, Costa Mesa, CA (US); Andrew Holland Smiley, San Diego, CA (US)

( * ) Notice: Subject to any disclaimer, the term of this patent is extended or adjusted under 35 U.S.C. 154(b) by 733 days.

(21) Appl. No.: 14/174,098

(22) Filed: Feb. 6, 2014

(65) Prior Publication Data
US 2014/0221779 A1    Aug. 7, 2014

Related U.S. Application Data

(60) Provisional application No. 61/761,295, filed on Feb. 6, 2013.

(51) Int. Cl.
*A61M 21/02* (2006.01)
*A61B 5/0484* (2006.01)
(Continued)

(52) U.S. Cl.
CPC ........... *A61M 21/02* (2013.01); *A61B 5/0482* (2013.01); *A61B 5/0496* (2013.01);
(Continued)

(58) Field of Classification Search
CPC . A61B 2560/029; A61B 5/002; A61B 5/0482; A61B 5/04842; A61B 5/04845;
(Continued)

(56) References Cited

U.S. PATENT DOCUMENTS

| 4,735,199 A | 4/1988 | DiLulio |
| 4,836,219 A | 6/1989 | Hobson et al. |

(Continued)

FOREIGN PATENT DOCUMENTS

| AU | 2002302195 | 6/2002 |
| AU | 2004229117 | 4/2004 |

(Continued)

OTHER PUBLICATIONS

AASM manual for scoring of sleep and associated events, Amer. Academy of Sleep Medicine, 2007, AASM Westchester, IL. (57 pgs.).

(Continued)

*Primary Examiner* — Christopher D Koharski
*Assistant Examiner* — Pamela M Bays
(74) *Attorney, Agent, or Firm* — Robert C. Kain, Jr.

(57) ABSTRACT

Dream stage enhancement uses a headband with EEG-EOG sensors, onboard processors, memory, coarse and fine time REM waveform detection modules, LEDs and an audio playback unit. After normalization to the user's EEG waveforms, the user's EEG-EOG signals are processed, REM and NREM stages detected and light, sound or AV stimuli are presented to the user based upon user-supplied light-sound-AV stimuli commands. To provide a reality check control ("RCC"), the head unit has a user actuatable RC interface whereby during sleep, RC stimuli are presented when the user depresses the RCC control which plays back the user supplied stimulus. In a "learning mode," the user selects "Recall" or "No Recall" ("NR") after the sleep period. If NR, then the system changes the color of light stimuli, light intensity, flash, audio sound type, audio intensity, and AV. If "Recall" the user supplied stimuli commands are carried out.

8 Claims, 15 Drawing Sheets

(51) Int. Cl.
*A61B 5/00* (2006.01)
*A61B 5/0496* (2006.01)
*A61B 5/0482* (2006.01)
*A61M 21/00* (2006.01)

(52) U.S. Cl.
CPC ...... *A61B 5/04842* (2013.01); *A61B 5/04845* (2013.01); *A61B 5/4806* (2013.01); *A61B 5/4812* (2013.01); *A61B 5/002* (2013.01); *A61B 2560/029* (2013.01); *A61M 2021/0027* (2013.01); *A61M 2021/0044* (2013.01); *A61M 2021/0072* (2013.01); *A61M 2205/3303* (2013.01); *A61M 2205/3561* (2013.01); *A61M 2205/3569* (2013.01); *A61M 2205/3584* (2013.01); *A61M 2205/3592* (2013.01); *A61M 2205/52* (2013.01); *A61M 2205/581* (2013.01); *A61M 2205/584* (2013.01); *A61M 2209/088* (2013.01); *A61M 2210/06* (2013.01); *A61M 2230/10* (2013.01); *A61M 2230/14* (2013.01); *A61M 2230/18* (2013.01)

(58) Field of Classification Search
CPC ... A61B 5/0496; A61B 5/4812; A61B 5/4806; A61M 2021/0027; A61M 2021/0044; A61M 2021/0072; A61M 2021/0022; A61M 2021/02; A61M 2230/10; A61M 2230/14; A61M 2230/18
USPC ......................................................... 600/301
See application file for complete search history.

(56) References Cited

U.S. PATENT DOCUMENTS

| | | | |
|---|---|---|---|
| 4,863,259 A | 9/1989 | Schneider et al. | |
| 5,101,831 A | 4/1992 | Koyama et al. | |
| 5,280,791 A | 1/1994 | Lavie | |
| 5,495,853 A | 3/1996 | Yasushi | |
| 5,507,716 A * | 4/1996 | LaBerge | A61M 21/00 600/27 |
| 5,551,879 A * | 9/1996 | Raynie | A61M 21/00 434/236 |
| 5,709,645 A | 1/1998 | Siever | |
| 5,954,629 A | 9/1999 | Yanagidaira et al. | |
| 6,443,977 B1 | 9/2002 | Jaillet | |
| 7,637,859 B2 | 12/2009 | Lindback et al. | |
| 7,727,139 B2 | 6/2010 | Topp et al. | |
| 7,956,756 B2 | 6/2011 | Kubey et al. | |
| 8,213,670 B2 | 7/2012 | Lai | |
| 8,267,851 B1 * | 9/2012 | Kroll | A61M 21/00 600/26 |
| 8,303,635 B2 | 11/2012 | Hurst | |
| 8,382,484 B2 | 2/2013 | Wetmore et al. | |
| 8,562,659 B2 | 10/2013 | Wells et al. | |
| 8,628,462 B2 | 1/2014 | Berke et al. | |
| 2006/0252978 A1 | 11/2006 | Vesely et al. | |
| 2009/0198145 A1 | 8/2009 | Chow | |
| 2011/0257467 A1 | 10/2011 | Clegg et al. | |
| 2013/0108995 A1 | 5/2013 | DePasqua et al. | |
| 2013/0303837 A1 | 11/2013 | Berka et al. | |

FOREIGN PATENT DOCUMENTS

| | | |
|---|---|---|
| AU | 2005202797 | 2/2006 |
| DE | 19920376 | 5/1999 |
| KR | 2013141269 | 6/2012 |
| RS | 20100004 | 8/2011 |
| WO | WO2013040642 | 3/2013 |

OTHER PUBLICATIONS

Induction of Lucid Dreams Systematic Review of Evidence, T. Stumbrys et al., Consciousness and Cognition 21 (2012) 1456-1475 (20 pgs.).

The NovaDreamer Lucid dream Mask: A review; at www.world-of-lucid-dreaming.com/lucid-dreamer.html (4 pgs.).

"Remee, The REM inhancing Lucid dreaming mask" by Bitbanger Labs, May 2012, Kickstarter http://www.kickstarter.com/projects/bitbangerlabs (6 pgs.)

"REM Dreamer Lucid dream induction device" REM Dreamer at http://remdreamer.com (2 pgs.).

"Lucid Dreaming App" by Alexander Stone, Feb. 20, 2012 at http://play.google.com/store/apps/details?id=com.lucid-dreamingapp.beta (3 pgs.).

"Lucid Dreamer" by Guardanis, Dec. 11, 2013 https://play.google.com/store/apps/details=id-guardanis.dreamer (3 pgs).

* cited by examiner

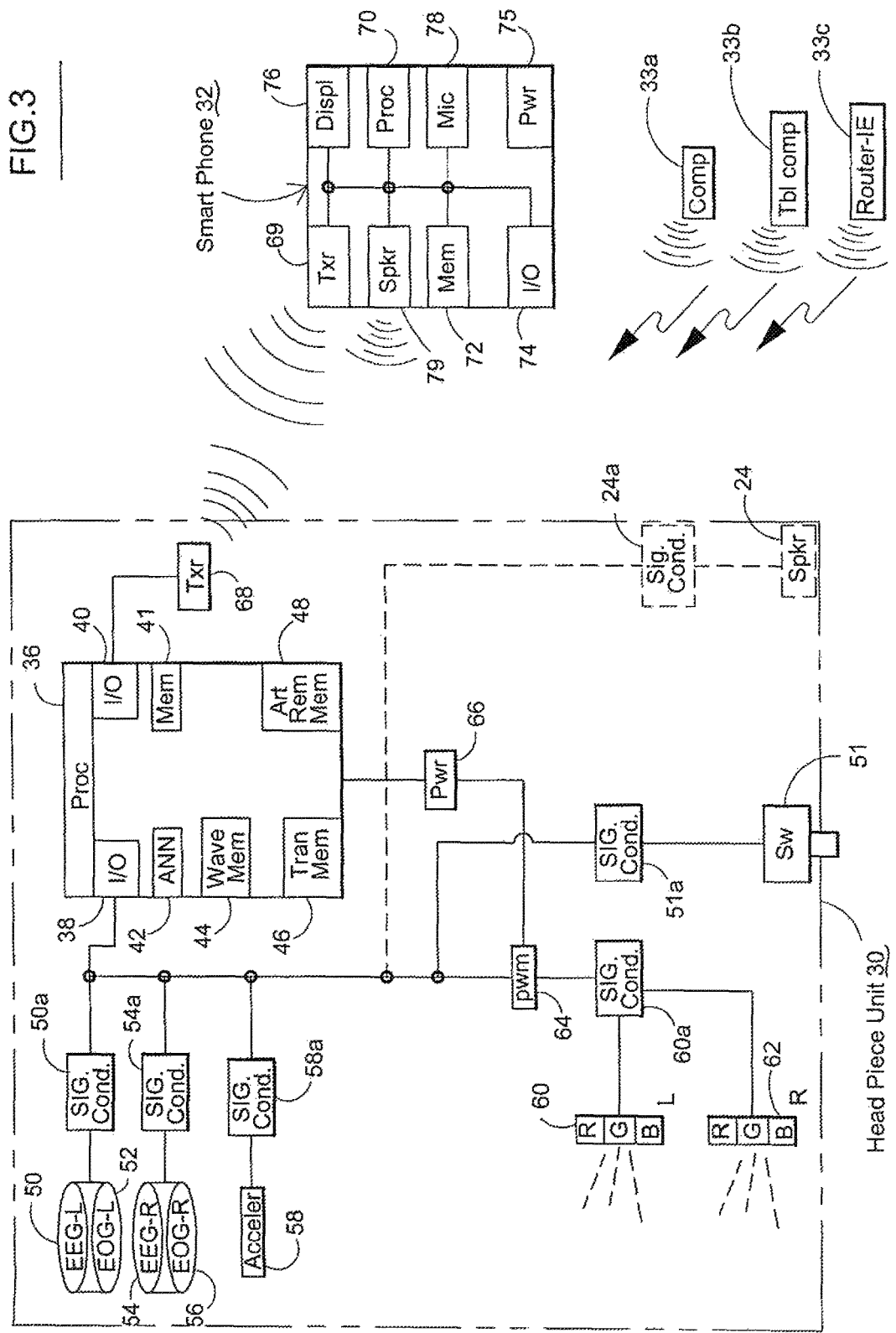

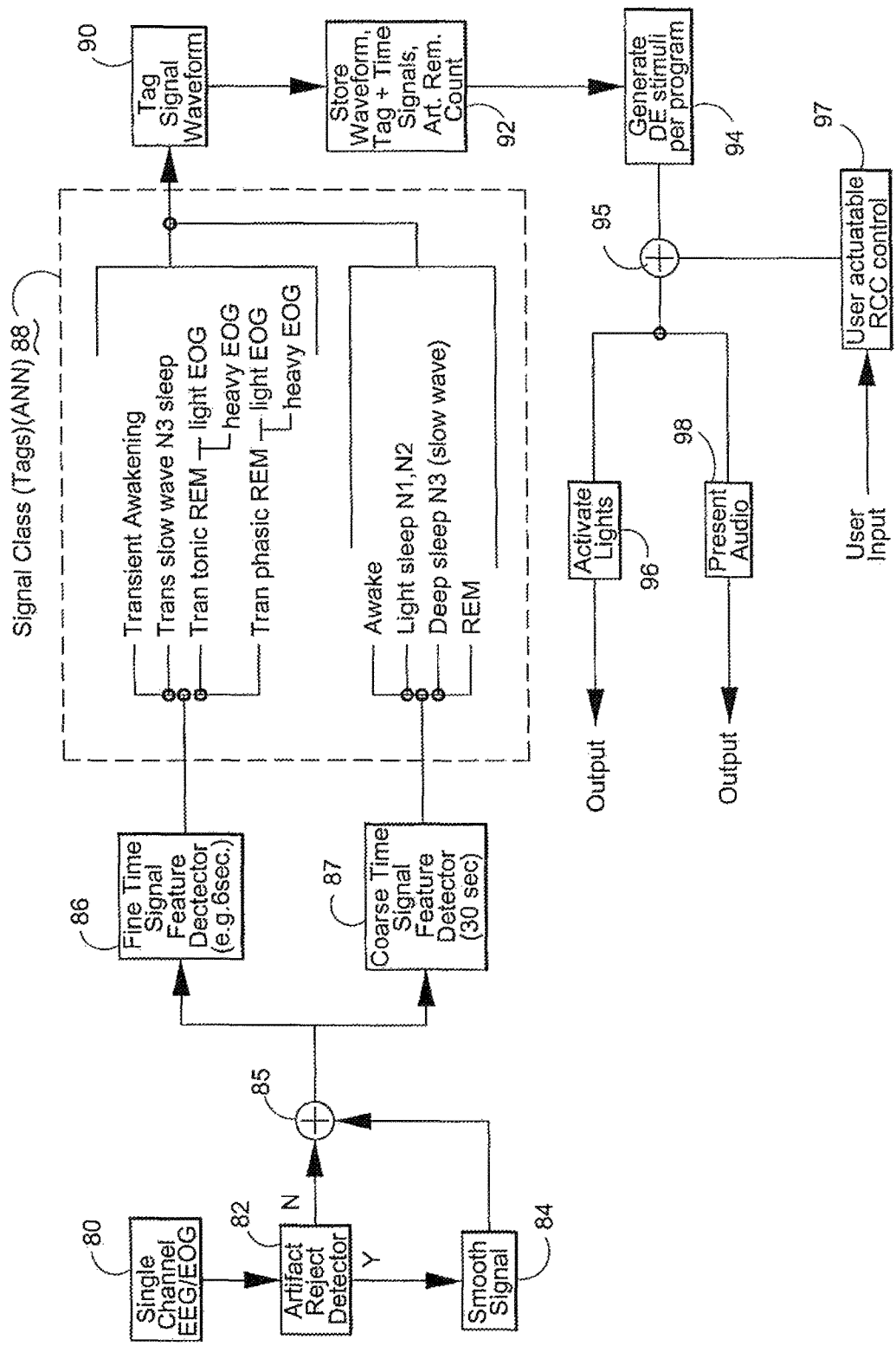

DREAM ENHANCEMENT APPARATUS AND METHOD

This is a regular patent application based upon and claiming the benefit of priority from U.S. provisional patent application Ser. No. 61/761,295, filed Feb. 6, 2013, the contents of which is incorporated herein by reference thereto.

The present invention relates to a method and a system for enhancing a user's dream stages.

BACKGROUND OF THE INVENTION

It is known that sensors can track brainwave activity (electroencephalography, or EEG) and eye movement activity (electrooculography or EOG) and overt body movements during the night. Dreams typically occur during tonic and/or phasic Rapid Eye Movement (REM) and sometimes during deep sleep (Non-REM2 (N2) or N3). See AASM Manual for the Scoring of Sleep and Associated Events, Amer. Academy of Sleep Medicine, 2007 Westchester, Ill.; see also Rechtschaffen A, Kales A, editors. Los Angeles: Brain Information Service/Brain Research Institute, University of California; 1968 (manual of standardized terminology, techniques and scoring system of sleep stages in human subjects). Slow wave sleep, characterized by high amplitude low frequency brain activity, is also responsible for dreams during which the user may be stimulated to enhance dreams or quality of sleep.

Sleep experts score sleep by sampling a user's EEG in 30 second epochs. Experts classify an epoch as one of the following stages of sleep or awake: nonREM 1 (lightest sleep N1), nonREM 2 (medium sleep N2), nonREM 3 (deep sleep N3), and REM. REM sleep is further split into phasic REM (where bursts of eye moments occur) and tonic REM. A sleep cycle generally lasts 90 minutes and a typical sleep cycle stage sequence is: N1, N2, N3, N2, N1, REM, repeat.

REM is the primary sleep stage of interest to users for dream enhancement, where dream enhancement refers to applications including but not limited to the presentation of subtle stimuli towards the subconscious modulation of dream content, or loud and overt dream signs, towards the goal of assisting lucid dreaming, also known as an EILDs (externally-induced lucid dreams). A lucid dream occurs when one becomes aware that they are dreaming. Lucid dreaming has been proven to improve quality of life through reducing nightmare frequency, stress and anxiety and also allows users to practice real life tasks in the dream world towards their improvement in waking life. See Spoormaker V, I, van den Bout 3, "Lucid Dreaming Treatment for Nightmares: A Pilot Study" Psychother Psychosom 2006; 75:389-394; see also Spoormaker V, "A Cognitive Model of Recurrent Nightmares," International Journal of Dream Research 2008; Vol 1, No 1; and see Erlacher, D., & Schredl, M. (2010), "Practicing a motor task in a lucid dream enhances subsequent performance: A pilot study," Sport Psychologist, 24(2), 157-167 and "Applied Research Practicing a Motor Task in a Lucid Dream Enhances Subsequent Performance: A Pilot Study." Eye movements are not affected by sleep paralysis and sleep scientists first used pre-agreed upon eye movements to prove the existence of the lucid dream state. Laberge, S. (1980), "Lucid dreaming: An exploratory study of consciousness during sleep," (Ph.D. thesis, Stanford University, 1980), (University Microfilms No. 80-24, 691).

U.S. Pat. No. 8,628,462 to Berka discloses a system for optimizing sleep patterns. EEG signals are monitored. REM and NREM sleep stages are identified. Pattern recognition techniques are used to identify these sleep states. Once the current sleep state is detected, and the current sleep state differs from the desired sleep state, then stimuli is applied to the user. An accelerometer is used to detect major physical movement of the user.

U.S. Patent Publication No. 2013/0303837 to Berka discloses a system for tailoring sleep architecture. The Berka '837 published application is a further enhancement to the system described in the Berka '462 patent. The system includes a mask to be worn by a user. The mask has one or more electroencephalograph (EEG) sensors, a visual element configured to generate light, an audio element configured to generate sound, and a sensor determine a current sleep state and a target sleep state.

U.S. Pat. No. 5,954,629 to Yanagidaira shows EEG sensors used to detect brain waves and to electrically stimulate such brain waves. U.S. Pat. No. 5,507,716 to La Berge discloses equipment used to provide low level sensory stimuli to a sleeping person so that he or she may become consciously aware that he or she is dreaming, while he or she continues to sleep and dream, thereby having lucid dreams. The system includes means to detect the eyelid movements; a low intensity light and sound stimuli; a face mask adapted to be worn by the sleeping person; and a data storage to receive signal data from the sensors and generate the light and sound signals.

U.S. Pat. No. 7,727,139 to Topp discloses a dream detection system having: a mask with an infrared sensor to detect REM sleep; an alarm to indicate REM sleep; a first transmitter; a first receiver; and a first processor in data communication with the sensor, alarm, mask transmitter, and mask receiver; and a control unit which is separate and distinct from the mask. The control unit has a transmitter for transmitting data to the mask receiver; a receiver for receiving data from the mask transmitter; an audio player; a speaker; and a sensor detecting REM sleep.

U.S. Pat. No. 8,267,851 to Knoll discloses an apparatus that induces a lucid dream in the brain of a subject. The circuit generates a brain state entrainment signal sufficient to cause a lucid dream in the brain of the subject by entrainment. A transducer applies electrical signals to the user's brain. The transducer uses an electrical waveform, a light waveform, and a sound waveform and a magnetic waveform. The brain state entrainment signal from the circuit applies the transducer waveform to the subject while the subject is awake.

OBJECTS OF THE INVENTION

It is an object of the present invention to provide a user programmable EEG based sleep staging for enhancing a user's lucid dream.

It is another object of the present invention to provide a user activated reality check sub-system to confirm or deny the existence of a dream sleep stage. The reality check subsystem is used to detect the presence of a dream state. It is the realization of that dream state which enables the lucid dream state.

It is an additional object of the present invention to provide a programmable device using light and/or sound to stimulate a certain sleep stage.

It is a further object of the present invention to provide a method for enhancing a user's lucid dream stage with device having a learning mode wherein the user inputs a "recall" command when the user remembers a stimuli induced dream element in a dream.

It is an additional object of the present invention to provide an apparatus for enhancing a user's lucid dream stage by utilizing a smart phone.

SUMMARY OF THE INVENTION

The present invention relates to a method for confirming a user's lucid dream stage and an apparatus for a similar purpose. A headband unit has electroencephalography (EEG) and electrooculography (EOG) sensors which are in contact with the user's skin. A plurality of light emitting devices (typically LEDs), mounted on the head unit, are directed towards the user's eyes to stimulate and illuminate the user's ocular senses with a plurality of distinct colored lights (including white light). In addition to the headband unit, the system includes an audio playback device which is linked to the head unit by a telecommunications network (typically BLUETOOTH™). The telecommunications network carries audio stimuli commands from the head unit to the audio playback unit. In the current embodiment, the audio playback unit is a smart phone which responds to the audio stimuli commands.

To normalize the EEG-EOG signals and create baseline REM stage, NREM1 stage; NREM2 stage, NREM3 stage data, the head unit obtains EEG and EOG signals over a plurality of sleep periods (in a current embodiment, 12 nights of base data). The head unit (currently with an artificial neural network module) creates normalized data representative of the user's REM, NREM1, NREM2, and NREM3. The neural network may be replaced by waveform detection modules.

Prior to a designated sleep period, the user selects certain light or sound or AV stimuli for the sleep stages, mainly the REM stages. In the current embodiment, the user inputs stimulus commends into the smart phone user interface.

During the designated sleep period, the headband unit detects a REM sleep stage based upon the then acquired EEG and EOG signals and the normalized data and generates a REM indicator signal. The REM indicator is a time-based signal which, if displayed to the user via the smart phone is overlaid atop the EEG signal. In an enhanced system, artifacts are removed from the EEG-EOG. The headband unit has a accelerometer which is used to detect the user's physical movements and electronic sub-module to remove these artifacts from the EEG-EOG signal. The accelerometer is used to track overt movements (i.e. awakening) and small head-jerks which may occur during REM stages.

Light or sound or light and sound stimuli are presented to the user in the presence of said REM indicator and based upon the lucid stimuli commands. Audio stimuli commands are sent over the telecommunications link from the headband unit to the audio playback device (in one embodiment, the smart phone) and the device plays back sounds.

In a further enhancement, the method and the system includes a reality check control ("RCC"). The user programs reality check (RC) stimuli commands into the head unit. The head unit itself has a user actuatable interface (like a switch or touch sensor) which, when depressed or activated, causes the device to present the RC stimuli. The theory is that the user should depress the RCC control when the user believes that he is in a dream state. Since the user has pre-programmed the RCC stim ("RC stimuli"), if the user does not recognize the RC stim, which is a version of the DE stim ("Dream Enhancement stimuli"), then the user is in a dream stage. If the user recognizes the RC stim, then the user is awake.

In an enhanced version of the invention, after the sleep period, the user can check the EEG wave signal train, with the overlaid REM indicators and the RC stimulus ("RC stim") indicator. The user may recall depressing the RC stim control and the RC stim indicator is shown in the EEG wave signal train.

The method and system detects REM sleep stage over an 30 second epoch in a coarse time waveform detection module and over a shorted predetermined time-based window (less than 15 seconds, and currently at 6 seconds). The system detects REM sleep the 30 second coarse time epoch and the shorter fine time period with a plurality of REM indicator signals.

In an enhanced "learning mode" process, the user selects "a learning mode command." The system, in the learning mode, uses an initial set of lucid stimuli commands (which may be pre-programmed without the user's input), generates REM indicators and presents the initial set of lucid stimuli to the user. A user actuatable user interface is provided as a means for generating a lucid dream recall indicator signal. The user inputs "Recall" or "No Recall." In the presence of the recall dream indicator, the system has the user input one or more lucid dream stimuli commands and the system employs user-supplied lucid stimuli commands rather than the initial set of lucid stimuli commands. In the absence of the recall dream indicator, the system changes the color of the light stimuli, the light intensity, a flashing light stimuli, the frequency of the flashing light, an application of audio stimuli, the intensity of the audio stimuli and/or the sensory impact of the AV stimuli. If the user continues to depress "No Recall" (a continued absence of the recall dream indicator), the system incrementally changes the light, audio and/or AV stimuli until the recall dream indicator is present.

In another embodiment, the headband unit itself carries an audio playback module with a speaker and audio playback sound signals stored in the head unit.

The details of the system include an onboard processor, an onboard telecommunications module, onboard data memory store(s), and a programmable neural network. The user-supplied or the initial set of lucid stimuli commands are stored in the onboard memory. The onboard processor has a light activation module, operative with the processor and the data store, for actuating said light emitting devices (usually LEDs) in the presence of REM indicator signals and based upon the lucid stimuli commands. The processor also has an audio activation module which works with the audio playback device. The onboard processor sends audio stim commands, via the onboard telecommunications module, to the audio playback device or smart phone. The playback device emits sound to the user.

The smart phone user interface and display can be used to permit the user to input lucid stimuli commands. Also, the user can select to download signals representative of the user's EEG waveform and, optionally, overpay the REM indicia as time-based signals. Alternatively, the REM time based signals can be shown on a singular time line with the system generated lucid stimuli markers or indicators. In this manner, the user could see his REM signals and the system generated stim signals.

Optionally, the user can select an audio play of the REM indicia wherein the phone audibly announces the REM time based indicator and the time, and the DE stim, in the time-based order of the record.

BRIEF DESCRIPTION OF THE DRAWINGS

Further objects and advantages of the present invention can be found in the detailed description of the preferred embodiments when taken in conjunction with the accompanying drawings in which:

FIG. 3 diagrammatically illustrates a block diagram of one embodiment of the present invention consisting generally of the headband unit and a smart phone (additionally showing telecom connections with a computer, tablet computer and a router acting as an internet enabled (IE) device);

FIG. 4 is a diagrammatic block diagram showing signal processing flow charts and dream enhancement stimuli outputs (DE stim);

DETAILED DESCRIPTION OF THE PREFERRED EMBODIMENTS

Figure 2:
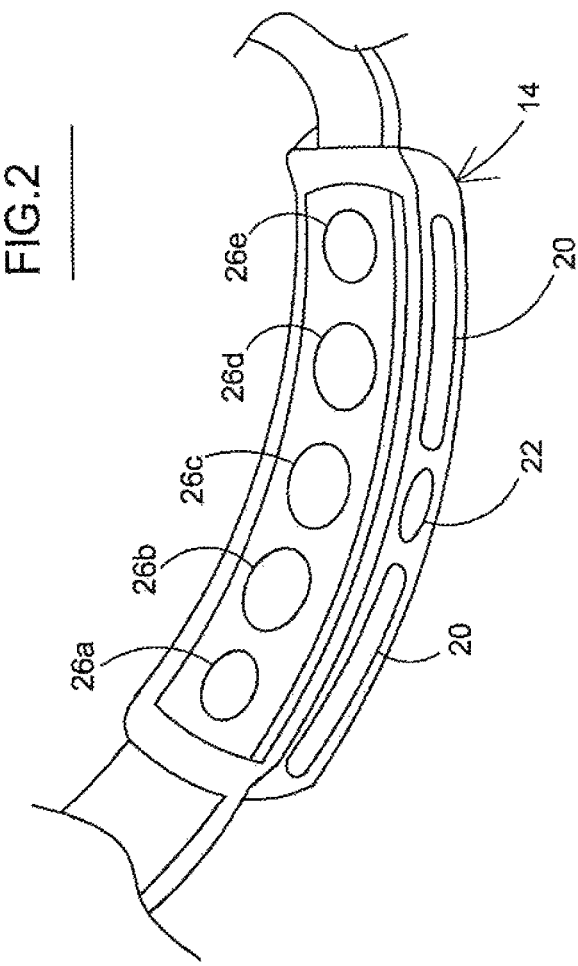
FIG. 2 diagrammatically illustrates the inboard surface of the headband unit showing EEG and EOG sensors and light stimuli bars.

The present invention relates to a method and a system for enhancing a user's dream stages. Similar numerals designate similar items in the drawings. Also, certain abbreviations are used in the specification and in the drawings and the Abbreviations Table near the end of this patent application sets forth some explanation of these abbreviations. Further explanations are found in the patent specification.

Some of the special features of the present invention includes: (1) a User programmable EEG-based sleep staging for lucid dreaming; (2) a device using a user-activated reality check sub-system to confirm or deny the existence of a lucid dreaming sleep stage; and (3) a programmable device using light and sound to stimulate a certain sleep stage.

Basic Theory

The present invention seeks to enhance dreams and improve the quality of a user's sleep. Sensors track brainwave EEG activity and eye movements EOG and overt body movements during the night and one or more algorithms distinguish the user's various sleep stages. The device and method specifically distinguishes the occurrence of (i) Rapid Eye Movement (REM) from (ii) Non-REM sleep stages (including slow wave sleep) and (iii) awakenings. The inventive system and method permits users to pre-select various sensory stimuli, which stimuli will be applied during different stages of sleep detected by the inventive device. In this manner, the user's dream state is enhanced or his or her sleep is improved. Slow wave sleep, characterized by high amplitude low frequency brain activity, is also responsible for dreams during which the user may be stimulated to enhance dreams or quality of sleep.

Potential uses for wearable technology with sleep stage tracking capabilities and light and sound stimulus generation are discussed below.

For dream augmentation, the user is presented with lights and/or sounds directed at the user to stimulate or supplement a dream. Dreams occur mainly in REM sleep, therefore when the sleep staging algorithm detects a tonic or phasic REM state, the device may, for example, deliver a very brief (for example a couple of seconds in length) green light strobe paired with a sharp crescendo sound effect over a brief period of time. During sleep, many external stimuli may bombard the senses, but the brain often interprets the stimulus and makes it a part of a dream to ensure continued sleep. See Antrobus, John (1993), "Characteristics of Dreams, "Encyclopedia of Sleep and Dreaming. The user—in his or her dream—will notice their preset custom light and sound cue, and these cues allow the user to realize he or she is dreaming, and, while staying asleep, can initiate a lucid dream.

Another dream augmentation use of the inventive system and method includes delivery of stimuli for the subtle presentation of dream content. For example, users interested in dreaming about playing at the NCAA FINAL FOUR™ might choose basketball courts sound effects during a dream to help transform their dreamscape. Once the device detect a tonic or phasic REM state, the sound stimuli is applied to the user.

Since general sleep stage information is first stored onboard the headband unit, then uploaded to the SmartPhone, some users may want to know how long they spend in deep sleep versus light sleep versus REM sleep. The dream enhancement device records these sleep states for later analysis by the user or professional.

Another useful feature of the device and method is a smart alarm clock which detects a prescribed sleep stage and then issues a pre-set alarm presented to the user. To avoid sleep inertia, users should be awoken during a light sleep stage. Users set a period they want to be awoken and the device will wait until a N1 or REM epoch to awaken them. For example, the user may select an N1 or REM epoch which arises at anytime during the hours of 6:30 AM and 7:15 AM. If the device detects a N1 or REM epoch between 6:30 AM and 7:15 AM, an alarm is presented to the user to awake the user.

The smart alarm clock awakens sleepers at the opportune moment in their sleep cycle. People who are awakened during deeper sleep stages (such as N3) feel groggier and less refreshed than those who awake during lighter sleep stages (N1). This sleep disturbance is known as sleep intertia. See Tassi, P.; Muzet, A. (2000). "Sleep inertia," Sleep Medicine Reviews 4 (4): 341-353, doi:10.1053/smrv.2000.0098, PMID 12531174; see also Wertz, A. T.; Ronda, J. M.; Czeisler, C. A.; Wright Jr, K. P. (2006). "Effects of Sleep Inertia on Cognition," JAMA: the Journal of the American Medical Association 295 (2): 163-4. doi: 10.1001/jama.295.2.163, PMID 16403927. With the smart alarm, users set a period of time to be awoken, and when lighter sleep stages are detected during this period, preferably following a deep sleep and REM cycle, the alarm triggers ON.

The user may want to be awaken by an alarm on or about 6 AM. She may set the "alarm sleep window" to be 5:45 AM to 6:15 AM. The new device will trigger an ALARM ISSUED light/sound at any time within the alarm sleep window. An optimal point to be "alarmed awake" is at N1 or REM sleep stage.

Enhancement of deep sleep is another use of the inventive device and method. Deep sleep is the most regenerative and restorative stage of sleep. Studies have shown, among other interesting findings for deep sleep enhancement, that stimuli presented during slow wave sleep that the user associates with the learning of some task will improve performance on that task during his or her waking life. See Rudoy J., et. al. "Strengthening Individual Memories by Reactivating Them During Sleep," Science 20 Nov. 2009: Vol. 326 no. 5956 p. 1079 DOI: 10.1126/science.1179013.

Another example of a potential use of the inventive device is to maintain a vigilant, non-sleep state during life-threatening tasks. For example, truck drivers who need to stay awake for extended periods might set the device to warn them if they begin to trend towards a light sleep phase (N1). The headband can be worn while the user is awake and be set to detect this light sleep phase and cause an "AWAKE" alarm stimuli to be presented to the user.

Dreams typically occur during tonic and/or phasic REM and sometimes during deep sleep (N2, N3). Slow wave sleep, characterized by high amplitude low frequency brain activity, is also responsible for dreams during which the user may be stimulated to enhance dreams or quality of sleep.

The device (a) rejects artifacts caused by the user's gross physical movements then (b) identifies sleep stages during sleep epochs per a classification system; and then (c) for REM sleep cycles, generates lights or sounds or both light and sounds—which generation may be programmable by the user. Sometimes the dream enhancement stimuli is referred to a "DE stimuli" or "DE stim" as the system generates lights or sounds or both light and sounds (A-V) keyed to the detected signal patterns.

The smart phone is used to generate sounds and to configure the settings for the processed signals. Currently the EEG/EOG signals are processed on the headband unit in a circuit configured as an ASIC (Application Specific Integrated Circuit). The SmartPhone can be programmed to gather the headband unit's stored sleep data via a BLUETOOTH™ communications link and collect one night's sleep data. Any wireless telecommunications system may be utilized in other embodiments of the invention.

An embodiment of the present invention includes a headband that measures the user's Electroencephalography (EEG) and Electrooculography (EOG) activity directly via stainless steel active dry electrodes. The headband unit is worn above the eyes and about the upper part of the skull of the user. See FIG. 1. An onboard accelerometer (in the headband unit) measures head movements from the user's forehead. The headband also contains embedded red, green and blue LEDs capable of a full color spectrum via pulse-width modulation. The embedded LEDs are directed towards the eyes of the user. Other light systems, directed at or towards the user's eyes, may be employed. In one embodiment, data is wirelessly transmitted to a BLUETOOTH™—enabled client device (e.g. smartphone application). The automatic sleep staging algorithm which detects REM sleep is onboard the headband unit. Once detected, the headband's LEDs are flashed in concurrence with sound stimuli played from the client's smartphone device.

Automatic Sleep Staging Algorithm

The standard to locate a sleep stage, sometimes called "sleep scoring," is a 30-second moving time window. The 30 second sleep stage is called an epoch. The sleep stage primarily uses EEG data to detect the classified stage. Experts have a 80-90% confidence level in designating sleep stages during the selected 30-second scoring epochs.

In one embodiment, an onboard artificial intelligence (AI) algorithm is trained to distinguish between the NON-REM sleep stages 1-3, phasic REM and tonic REM stages, and awakenings using single channel EEG/EOG data collected from the forehead with sensors located 2 inches apart, centered on the user's nasion. In one embodiment, the inventive AI sleep staging algorithm was compared to data collected at a clinic using polysomnogram (PSG) equipment.

Transient sleep events within an epoch (typically 30 sec) or spanning multiple epochs are tagged with the inventive sleep staging algorithm, which algorithm works on EEG/EOG data in real time. In a current embodiment, 12 nights of sleep data were collected at the clinic using the inventive headband and this data was used to train the AI sleep staging algorithm. A transient sleep event passes quickly into and out of existence in the EEG-EOG signal stream. The transient sleep tags are overlaid on the sleep data.

The AI sleep staging algorithm detects: (a) NON-REM sleep stage 1 (N1), (b) NON-REM sleep stage—2 (N2) (c) NON-REM sleep stage—3 (N3), (d) phasic REM stage and (e) tonic REM stage, and (f) awakening.

Since users may have different sleep patterns, the inventive device may need AI training with the selected user in order to more accurately detect the sleep stage. Some users have deep sleep periods. Other users may have many awaking events. Some users have sleep stage sequences of N1, N2, no N3, etc. (the sequence being N1, N2, N1, pREM, tRem, N1, N2, N1, etc.).

The automatic sleep staging algorithm has an artifact rejection algorithm and two additional modes of operation. The 2 "sleep stage detection" modes are (a) fine-time detection mode (a preset time, anywhere between 3 sec. to 10 sec.) and (b) a coarse-time detection mode (30 sec, moving window). Classification of a detected sleep stage is made in either sub-system (fine time module (a) or coarse time module (b)) over the 30-second moving window epochs. These classified and detected sleep stages are classified effectively in real time. The term "real time" is meant to encompass real time signal acquisition and machine signal processing time (compared this type of "real time" processing and classification to post-processing the EEG/EOG signals hours after the user awakes).

Artifact Detection

The artifact-rejection algorithm removes signal components from the raw EEG/EOG signal that are too big to arise from brainwave or eye movement activity. This usually arises from overt body movements, jaw clenches or very heavy breathing. The output from the accelerometer detects gross head and/or body movements which create artifacts in the EEG/EOG signal streams.

The artifact rejection routine works as follows. If the raw EEG exceeds some threshold, center a window on that data, multiply it by a Hanning window of the same length and remove it the expanded window from the processed signal stream. Repeat the artifact rejection routine until the pre-processed data stream no longer exceeds the threshold. The number of times an artifact was subtracted from the data is stored as a feature in the waveform memory unit or the "artifact removed" memory unit.

Coarse-Fine Time Detectors

The coarse time mode classifies epochs into one of four (4) states: (1) Awake; (2) Light Sleep (N1/N2), N1 being lighter than N2; (3) Deep Sleep (N2/N3), N2 being lighter than N3; and (4) REM. The coarse time module algorithm in one embodiment operated at 80% accuracy compared with clinically captured, post acquisition signal processing results.

The fine-time algorithm uses shorter temporal segments to distinguish certain transient sleep events including awakenings, slow wave sleep, tonic REM periods, and phasic REM events grouped into segments with light and heavy eye movements. When these detected transient sleep events, grouped into segments in the moving window epoch, match the predetermined sleep stage threshold(s), the sleep stage classification module activates the user-programmed or the pre-programmed light, sound or light-and-sound output. The AI sleep stage algorithms also detect slow wave sleep which is, during N3 stage, a high amplitude, low frequency EEG.

The fine-time algorithm may be tuned to any temporal window and some of the window lengths simulated in the current embodiment have been 3 sec, 5 sec, 6 sec, and 10 sec. In one embodiment, with a 6 second segment, the fine time algorithm performed with 75% accuracy in a 5-way classification between the following transient events: 1) Slow wave sleep; 2) Tonic REM; 3) Phasic REM—light eye movement activity; 4) Phasic REM—heavy eye movement activity; and 5) Awakening.

The Coarse Time algorithms and the Fine Time algorithms use the same waveform feature detection algorithms in the classification routine and in the artifact rejection routine. The fine and coarse detectors effectively use the same signal feature extraction algorithms. Sometimes these signal feature detection algorithms are called dimensionality reduction waveform algorithms. These feature extraction algorithms for EEG/EOG signals are known in the art as a methodology to classify sleep stages from the EEG and EOG signals.

Feature extraction algorithms employ power spectrum bins spanning 03-30 Hz with 1-Hz bin width, Kurtosis, standard deviation and a number count of removed artifacts. A multilayer perception artificial neural network (ANN) is trained to classify between the required stage outputs using the above features as inputs. The ANN is trained using leave-one-out cross validation to simulate hypothetical algorithm performance on an unobserved night of data.

Programmable Settings

The user, via an API in his or her smartphone, may pre-select either a coarse detection related stimuli or a fine detection related stimuli. The user selection may also determine the frequency of the ouput stimuli.

For example given a sleep sequence of N1, N2, N3, N2, N1, REM, repeat, when the user pre-sets, prior to his or her sleep, the "lucid dream state" and the coarse detector at a 3-flash blue light stimuli (blue light flashed three (3) times) presented a stimuli from the headband unit to the user's eyes), THEN upon a 30 sec. epoch of REM, the system presents the 3-flash blue light. The user, because he or she remembers that a "3-flash blue" is a lucid dream state, will alter his or her sleep cycle to: N1, N2, N3, N2, N1, REM (system detected REM), then stimulated REM. This is an enhanced dream state.

Assuming different user pre-sets consisting of (i) select "lucid dream state" and (ii) select fine detector and (iii) select 3-flash blue light stimuli, THEN upon a 6 sec. time period of detected REM, the system presents the 3-flash blue light. The user, because he or she remembers that a "3-flash blue" is a lucid dream state, will alter his or her sleep cycle to: N1, N2, N3, N2, N1, REM (system detected REM), then REM. Without the stimulus, the sleep cycle is N1, N2, N3, N2, N1, REM, repeat.

The result of a "coarse detector selection" is: N1, N2, N3, N2, N1, REM (system detect 30 sec. REM epoch, trigger DE stimuli), then REM (IF system detects second 30 sec. REM epoch, trigger DE stimuli), then REM (IF system detects third 30 sec. REM epoch, trigger DE stimuli OR if no detect 30 sec. REM epoch, system does NOT trigger DE stimuli). Effectively, the user has programmed a 30 second DE stimuli assuming the user remains in the REM sleep stage.

The result of a "fine detector selection" is: N1, N2, N3, N2, N1, REM (system detect 6 sec. REM transient signal, trigger DE stimuli), then REM (IF system detects a second 6 sec. REM transient, trigger DE stimuli), then REM (IF system detects a third 6 sec. REM transient, trigger DE stimuli OR if no detect 6 sec. REM transient, system does NOT trigger DE stimuli). Effectively, the user has programmed a 6 second DE stimuli assuming the user remains in the REM sleep stage.

Of course, the user's sleep pattern may vary form the examples given above, but the above explanation provides examples of potential sequential operations of the dream enhancement ("DE") system.

Combinatory selections are also provided. For example, the user may select a coarse detector ON as an initial DE stim trigger, then program the DE system to transition to a fine time detector for the next REM sequential signal. The system sequence is as follows.

DE Stim Combo: Coarse detector selection in sleep stage sequence: N1, N2, N3, N2, N1, REM (system detect 30 sec. REM), then REM (IF system detects next sequential 6 sec. REM transient, trigger DE stimuli), then REM (coarse detector OFF and fine detector ON, IF system detects second sequential 6 sec. REM transient, trigger DE stimuli OR if no detect 6 sec. REM transient, system does NOT trigger DE stimuli).

To combine the smart alarm sub-system with the DE Stim Combo, the user pre-programs the DE system to be activated after certain clock time, such as after 6:00 AM. The resulting DE Stim Combo Clock is: (A) DE system stimulus OFF until after 6:00 AM; (B) after 6:00 AM, coarse detector ON in sleep stage sequence: N1, N2, N3, N2, N1, REM (system detect 30 sec. REM epoch, trigger DE stimuli), then REM (coarse detector OFF and fine detector ON, IF system detects next sequential 6 sec. REM transient, trigger DE stimuli), then REM (IF system detects second sequential 6 sec. REM transient, trigger DE stimuli OR if no detect 6 sec. REM transient, system does NOT trigger DE stimuli).

Reality Check Control

During a dream stage, the user is generally unsure whether or not the user is actually dreaming or is physically engaged in the perceived event. The "perceived event" is in the dream. The present invention has a "reality check control" or RCC. The RCC sub-system includes a button on the exterior, outboard surface of the headband (FIG. 1, item 22) which the user can depress during his or her sleep. When depressed, the RCC sub-system issues and presents a pre-set stimuli to the user. For example, the RCC stimuli may be set as a 3 second RED LIGHT ON stimulus. Since the user has pre-set the 3 sec RED ON light for the RCC prior to going to sleep, the user in a dream state may perceive a long "red light dreamscape" or "red illumination dreamscape." When the user perceives this "red light dreamscape," the user is unsure whether the redscape is a "perceived event" in the dream or is caused by external stimuli.

However, the user may then conduct a "reality check" by physically depressing the RCC button on the headband unit, thereby activating the 3 sec. RED LIGHT ON stimulus.

The user, by pre-programming the RCC stim (which is a version of the DE stim), knows what the RCC stim presentation looks and sounds like. If the user thinks he or she has depressed the RCC control but is not presented with the RCC stim, then the user is in a dream stage. If the user does recognize the stimulus, then the user is awake, and not in a dream stage.

Another aspect of the RCC is upon awakening. If the user awakes and (a) remembers the redscape but (b) does not remember the physical activation of the RCC, then the user has achieved a dream state because he or she remembers the redscape. If on the other hand the user awakes and (a) remembers the redscape but (b) DOES remember the physical activation of the RCC, then the user has NOT achieved a dream state.

Alternatively, if the user awakes and (a) remembers the redscape, (b) DOES remember the physical activation of the RCC, and (c) remembers a second redscape, then the user has achieved a dream state because he or she remembers two sequential redscape events. The "redscape" in the dream may take the form of a sunset or a flashing red traffic light.

The RCC sub-system either (A) overrides the artifact rejection ("AR") module or (B) turns OFF the AR module for a predetermined time period. The physical act of RCC control activation causes the signal artifact. If the AR sub-system is left active (an ON state), then the AR sub-system may delete EEG-EOG signal stream during the user's physical act of activating the RCC button.

In addition, the inventive system and method may include auto-calibration modules for the DE stimuli to be recognized and/or improved by the user. The EEG/EOG information is collected, either actively, before or after the user's sleep period, or passively during the user's sleep period, and the data is used with the DE stim device which automatically adjusts the intensity of light and/or sound, and adjusting the placement of stimuli within the REM episode (a timing event relative to the detected stim trigger), to best suit the user. The idea is that each user is unique and the user may be sensitive to external stimuli during REM at different thresholds and times.

System and Method Details

Figure 1:
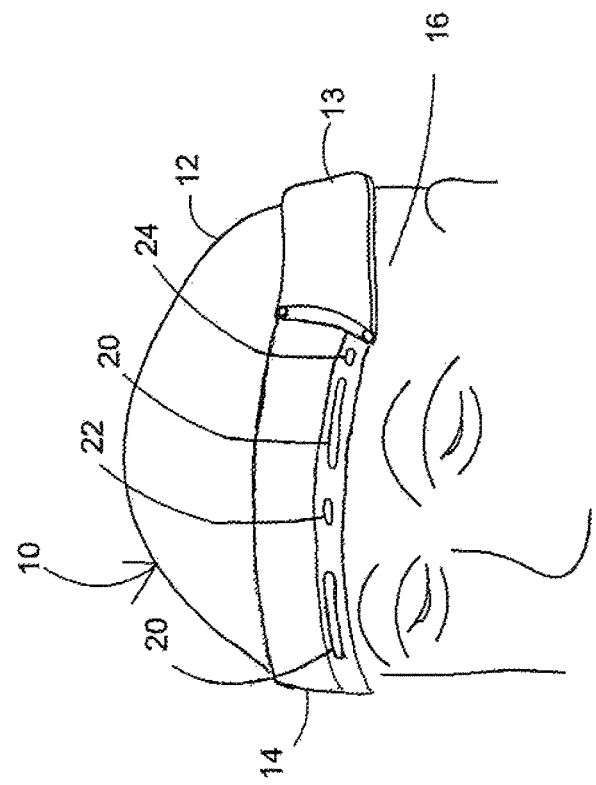
FIG. 1 diagrammatically illustrates the headband unit mounted on the skull and forehead of a user.

FIGS. 1-18 diagrammatically illustrate various embodiments of the present invention. In FIG. 1, a user's head 12 and forehead skull portion 16 is diagrammatically illustrated. The headband 10 includes headband unit 14. Headband unit 14 is strapped onto skull 12 by elastic headband member 13. Unit 14 is placed on the user's forehead 16.

Headband unit 14 includes light stimulation bars 20 (one bar positioned above the user's right eye and the second bar positioned above the user's left eye). Also, in the illustrated embodiment, a reality check control button 22 (or other actuator system such as a touch screen, heat sensor, etc.) is located at an intermediate position between light emitting bars 20. Button 22 can be used as any type of user actuated control. In a preferred embodiment, light emitting bars 20 may include a plurality of LEDs or other light emitting devices. Further, in an enhanced embodiment, a speaker system 24 is provided in headband unit 14. Although a majority of the description of the current embodiment of the present invention discusses the use of a smart phone for generation of sound stimuli (see FIG. 3), another embodiment of the present invention includes a speaker 24 or other audible presentation system as part of the headband unit 14.

FIG. 2 shows headband unit 14, the light emitting bars 20, the reality check control 22 and the plurality of EEG and EOG sensors 26a through 26e. The sensors are strategically placed in headband unit 14 such that the sensors are in skin contact with the user's forehead 16 or skull segment.

FIG. 3 diagrammatically shows a block diagram of one embodiment of the present invention. Headpiece 14 includes headpiece unit 30 which, in the current embodiment, is in telecommunications contact with smart phone 32. Smart phone 32, in a very simplified embodiment, is an audio playback device with a telecom linking module. The current embodiment uses smart phone 32 as a user command input device and a waveform and REM time-based marker display device. The illustrated telecommunications network is command carrying communications link between headpiece onboard transceiver 68 and telecom transceiver 69. In a preferred embodiment, this is a BLUETOOTH short range wireless communications link. Alternatively, or in addition to, computer 33a, or tablet computer 33b or an internet enabled IE device with a router 33c may be in a telecommunications link with headpiece unit 30. These supplementary electronic devices may provide supporting functionality to a simple audio playback unit.

Headband unit 30 includes a processor 36 coupled to input/output device 38 and input/output device 40. The processor is also coupled to various memory devices such as waveform memory 44, transient trigger memory 46 and artifact removal memory 48. The Abbreviations Table near the end of this patent specification provides additional details and explanations for the abbreviations in the drawings and specification. In addition, processor 36 operates in conjunction with an artificial neural network (ANN) 42 which is used to classify the dream stages having the waveform features discussed herein. The neural network 42 uses a plurality of normalization sleep periods in order to determine when the user has experienced a REM sleep stage, and the various NREM sleep stages. Twelve normalization sleep periods were used to train the ANN. These sleep periods are separated by extended user awake periods. Typically, during the day most users are awake and the daytime activity period is identified herein as an "extended user awake" period. Sleep periods are those periods between these daytime extended awake periods. The headband unit 30 and the current embodiment is an ASIC or application specific integrated circuit. However, discrete circuitry and micro processor circuits may be utilized. Some of the modules may be hardware, software, or may be logical circuits.

Rather than having discrete memory units 42, 44, 46, 48, a singular memory may be utilized in conjunction with processor 36. The discussion herein of discrete memory modules is to enable a reasonable explanation of the operation of the present invention. Memory modules may be directories or memory segments.

The EEG signals from the user's brain are picked up by left and right EEG sensors 50, 54. In the current embodiment, eye movement is detected by left and right EOG sensors 52, 56. The eye movement and the brainwave activity from sensors 50, 52 are supplied in a single channel EEG/EOG to signal conditioner 50a. The right side sensors 54, 56 are processed by signal conditioner 54a. In order to determine gross physical movement or awake periods, an accelerometer 58 is utilized as part of headband unit 30. The output from the accelerometer is conditioned by signal conditioner 58a. The processor 36 detects these signals from the signal conditioners and processes them through the neural network 52 and saves the pre-processed EEG and EOG waveforms in wave memory 44.

Ultimately, smart phone 32 can be programmed to obtain, via a upload from onboard processor 36, the waveforms from the onboard memory via telecom modules 68 and 69. The transient REM signals (time-based markers or indicators) and the coarse time awake, light sleep and deep sleep and REM signals are saved in transient memory 46 as time-based signals. Of course, a person of ordinary skill in the art could combine the waveform EEG-EOG signals from waveform memory 44 and add the transient time-based signals or time-based markers from memory 46 into a single data object. Artifact removal memory 48 carries artifact information (artifact count) derived from the accelerometer 58 and the EEG-EOG signals in order to determine a physical artifact. This artifact removal is explained above.

Headband unit 30 includes power supply 66 such that unit is substantially independent. In other words, headband unit 30 does not have wires or other items that would interfere with the user's sleep. Power is supplied to all circuit elements even though in FIG. 3 the illustrated power line only is applied to the pulse width modulating (PWM) circuit 64.

Once a REM or other dream stage is detected by processor 36, if the processor is programmed for particular lucid stimuli command, colored lights from LEDs 60, 62 are directed to the ocular senses or eyes of the user. LEDs 60, 62 include red, green, blue, full spectrum lights therefore the term "different colored light" refers to both white light as well as other colors detectable by the user's eyes. LEDs 60, 62 are supplied signals by signal conditioner 60a. Therefore, as generally discussed above, processor 36 accepts signals from the EEG/EOG sensors and processes those signals through the neural network 42 in order to detect dream stages of REM and NREM 1 to 3. Once normalized signals are obtained (typically 12 nights in the present embodiment), base line data is utilized which baseline data is representative of the user's REM. The detection algorithms may be set to detect these REM and NREM signal stages. The baseline data is compared to realtime acquired EEG-EOG signal streams to detect REM and NREM events.

Prior to any particular sleep period selected by the user (a "designated" sleep period), the user may input lucid stimuli commands which commands are translated into either light stimuli or audio stimuli or both audio/visual (AV) stimuli. Therefore, during the designated sleep period the real time REM sleep stage is detected by the neural network and a REM indicator signal is generated by the system. When the REM indicator signal is generated (this is either the transient signal identified in FIG. 4 or the coarse time REM signal), the processor 36 generates lucid stimuli commands which cause LEDs 60, 62 to emit the correct colored light in the correct intensity. The color and intensity are programmed generally by the user as lucid stimuli commands. If the user has programmed audio commands, the audio commands are processed by processor 36 which activates input/output module 40 and onboard transceiver 68. Transceiver 68 sends a signal representative of the audio stimuli command to smart phone 32 and transceiver 69. Smart phone 32 then activates accesses its audio playback memory and the audio speaker 78 which presents audible sound to the user during his or her REM sleep stage.

It is not necessary that entire smart phone be utilized because any audio device with a command carrying telecommunications link could be utilized. The important feature is that the audio device (smart phone 32) recognize the audio stimuli commands from the telecommunications link and then activate speaker 79 to present the pre-programmed sounds to the user.

Smart phone 32, in addition to transceiver 69, includes a display module 76 (the display or touch screen portion of the phone), processor 70, microphone 78, speaker 79, memory 72, and input/output module 74. Memory 72 includes a playback memory. The smart phone includes a power module 75 powering all the circuits. If smart phone 32 is a simple audio playback device, it also has a audio playback data store which is memory 72 and device telecommunications module 69 permits the audio stimuli command to be received from onboard transmitter 68 of headband unit 30. Smart phone 32 has a program interface for actuating the audio playback device in the presence of the REM indicator signal transferred between transceiver 68, 69.

Further, in a current embodiment, smart phone 32 has an input module which enables the user to input lucid stimuli commands. These lucid stimuli commands are first stored in device memory 72 and then downloaded to the onboard telecommunications module 68 and stored by processor 69 in onboard memory 41. The smart phone carries, in memory 72, program modules such that the user can program the operation of the headband unit and view unit 30 outputs.

Rather than neural network 42, the processor 46 may have a pattern detection modules that are diagrammatically illustrated in FIG. 4. Operationally, ANN 42 includes pattern detection modules. Further, in order to have the user review the sleep activity as EEG/EOG waveforms, processor 36 and memory 41 may have a upload program which permits the user, from smart phone 32, to command headband unit 30 to upload the EEG and EOG waveform patterns to device memory 72 as well as the time-based marker data for REM, and NREM 1 to 3 sleep stages. As stated earlier, the time-based markers or transient signals may be separately indicated or may be displayed atop the EEG waveforms. The smart phone has a smart phone memory data store 72. Processor 70 has a program module acting as a means for accepting and storing the EEG as time-based marker data into memory 72.

In an alternate embodiment, headband unit 30 may include speaker 24 (FIG. 1) and speaker signal conditioner 24a which is activated by processor 36 and memory 41 to generate audio stimuli based upon the user input lucid stimuli commands. Memory 41 would include audio playback data. In some instances, initial lucid stimuli commands are presented which are pre-programmed into unit 30 (rather than input by the user as discussed later herein).

In an enhanced embodiment, the headband unit 30 includes a reality check control (RCC). The reality check control enables the user to depress a headband switch 51 or user actuatable device 51 (touch screen, thermal sensor, etc.) when the user wants to test whether he or she is in a dream stage. The output from user actuated device 51 is conditioned by signal conditioner 51a. When the user depresses reality control switch 51, a RCC time marker is placed in memory 41 and in transient memory 46.

Since the user has pre-programmed the RCC stim, the user can recognize the stimulus. If the user believes that he or she depressed the RCC control but the user does not recognize the RCC stim, then the user is asleep in the dream REM stage. If the user recognizes the RCC stim, then the user is awake and not dreaming.

Alternatively, the user may check the recorded EEG-EOG signals via the smart phone. If the RCC time marker relatively closely matches a REM cycle or a REM stimuli or another dream stage marker, then after the user awakes and views the signal train, the user can make a visual determination that he or she triggered the RC stim. When the user views the EEG signals and RCC time marker time display via a smart phone 32, the user can be assured that he or she was subject to a dream that was (a) stimulated by headband unit 30 and (b) confirmed by the RCC. If on the other hand, the user believes he or she did strike the RCC actuator control 51, but upon review of the EEG signals on smart phone 32 there is no RCC time marker near the REM marker (or other dream stage marker), then the user recognizes that headband unit 30 issued a stimuli and the program automatically generated stimuli to cause the dream rather than the user actuated RCC stimuli control.

Persons of ordinary skill in the art can recognize that most of the functional elements of smart phone 32 can be deployed in computer 33a, tablet computer 33b or any internet enabled device 33c via a router operating over the telecom network.

FIG. 4 diagrammatically illustrates the basic flowchart and process method for processing the EEG signals. A single channel EEG/EOG signal is obtained in step 80. In step 82, the system detects artifacts by a detector. The artifact detection routine is discussed above. If an artifact is detected, the system executes a smooth signal function 84 and the EEG signal is smoothed by removal of the artifact. If an artifact is not detected, the NO branch is taken from rejection detector 82 and the process moves to summation point 85. The AR count is incremented in memory.

The pre-processed signal from summation point 85 is fed to both a fine time signal feature detector 86 and a coarse time signal feature detector 87. Fine time detector 86 operates over a pre-determined time-based window which is less than 15 seconds. In contrast, coarse time feature detector 87 operates on the more standard 30 second epoch time frame. In the illustrated embodiment in FIG. 4, the time window for fine time feature detector 86 is set at 6 seconds. This time window may be 6, 8, 10 or 15 seconds. As stated above, the feature extraction algorithms utilized in detectors 86, 87 are substantially the same. The outputs from the signal detectors 86, 87 are classification or tagged with a signal class from the artificial neural network. The signal classes are diagrammatically shown in class box 88. Therefore, fine time feature detector 86 generates: a transient awakening signal or time marker, a transient slow wave N3 sleep marker, a transient tonic REM signal which is further broken down into light EOG and heavy EOG. Further, the fine time feature detector 86 generates a time-based marker as a transient phasic REM signal further differentiated as a light EOG and a heavy EOG.

The coarse feature detector 86 generates an awake signal, a light sleep N1, N2 signal marker, a deep sleep signal or slow wave signal for sleep stage N3, and an REM time-based marker. The outputs from the artificial neural network are sent to functional block 90 which tags the signal waveform. The time-based tags may be overlaid on the smoothed EEG waveform. As indicated above, the EEG/EOG signal after it has been smoothed by artifact removal, may have an overlay which includes the time-based markers showing the coarse time REM (30 second window signal analysis) or the more transient tonic REM or phasic REM (fine time markers).

In function block 92, the waveforms are stored, the tags are stored and the time-based tag signals are stored. Also, the artifact rejection count is stored in the appropriate memory location. After the storage, the onboard processor generates dream enhancement or DE stimuli ("DE stim) in function block 94. The output from DE stimuli block 94, after the summation point 95, is applied to activate light module 96 or "present audio" module 98. The outputs from activate light module 96 are applied to the signal conditioners for the onboard light emitting devices which can be LEDs or other types of lights. The output from "present audio" module 98 is, in the current embodiment, an audio stimuli command applied to the onboard transmitter 68 which audio stimuli command signal is received by receiver 69 in smart phone 32. Speaker 78 then plays the recorded sound from memory 72 as required by processor 70, all in smart phone 32 and all based upon the audio stimuli command. In an enhanced embodiment when the speaker is onboard the headband unit 14, (see speaker 24 in FIG. 1), the "present audio" module 98 activates the signal conditioner and memory 41 for speaker 24. The signal conditioner is 24a and speaker 24 is shown in FIG. 3.

As described above, the headband unit 14 includes a user actuatable surface or switch 22 which provides a reality check control RCC control. Module 97 in FIG. 4 shows that the user supplies an input which activates the RCC control. The RCC control then triggers operations in processor 36 and memory 41 to generate RCC pre-programmed stimuli applied to the user. This may be light, or sound or combination such as AV stimuli. In the event AV stimuli is part of the RCC pre-programmed or user programmed stimuli command, then both light module 96 and audio module 98 are activated.

Figure 5:
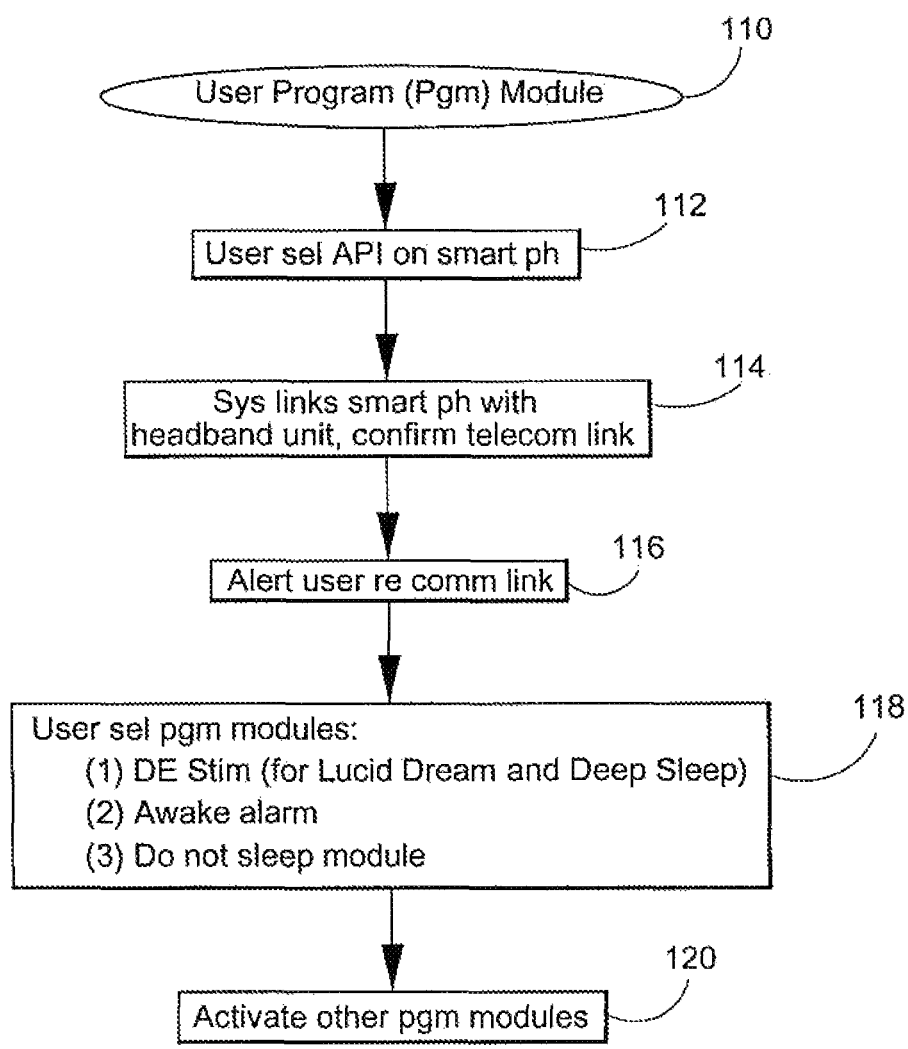
FIG. 5 provides a flowchart for the user program module.

FIG. 5 diagrammatically illustrates the basic user program 110 for the present invention. In step 112, the user selects an app or an API on a smart phone. This app is used to initialize head unit 14. In step 114, the system and onboard processor 36 links the smart phone with the headband unit 30 and confirms the telecom link. In step 117, the user is alerted that the comm link has been established. This may be by blinking light or other audio or visual cue. In step 118, the user selects various program modules such as details for dream enhancement stimulation program (DE stim) for lucid dream and deep sleep, or the awake alarm or the "do not sleep" module. In step 120, the system activates other program modules.

Figure 6:
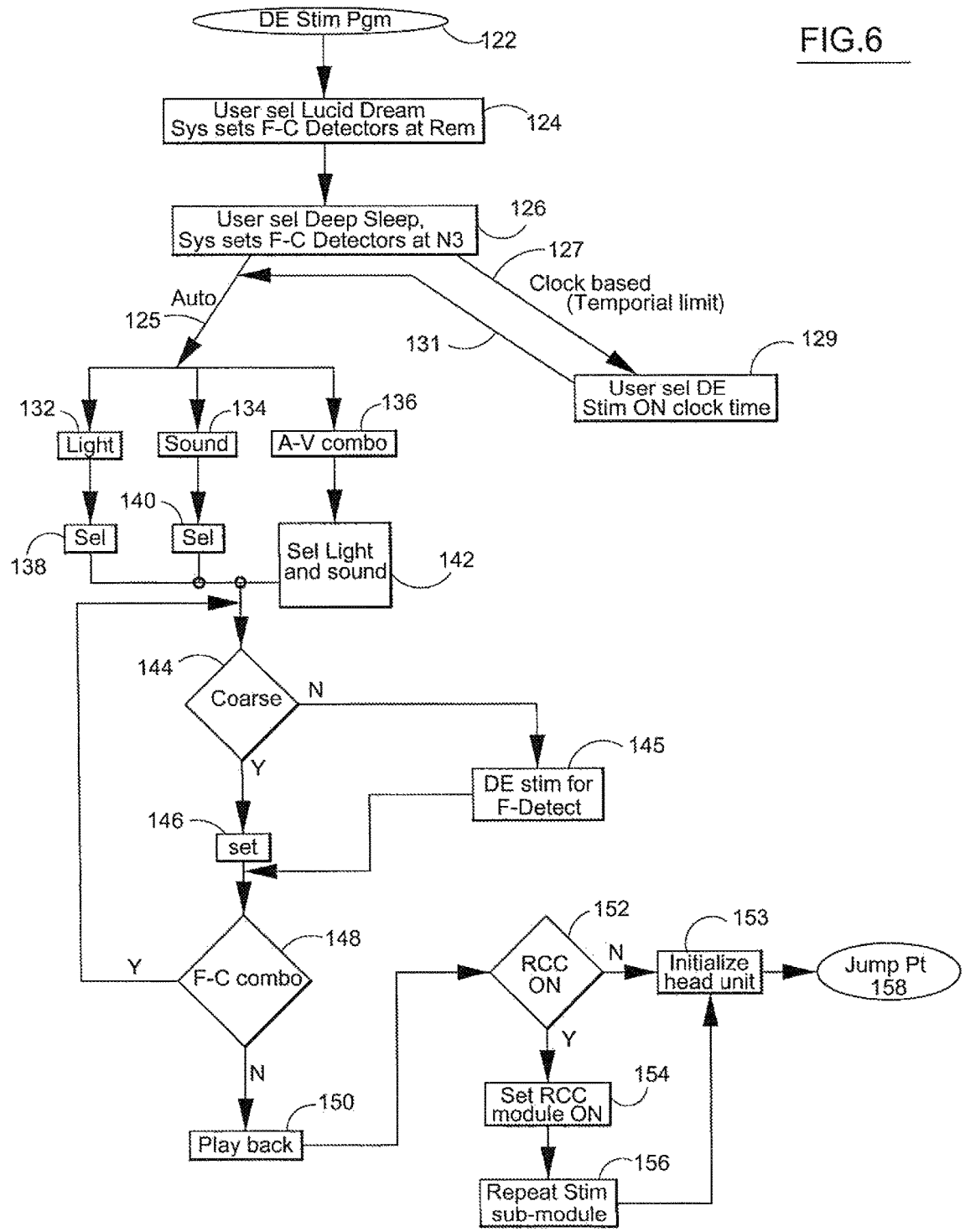
FIG. 6 provides a flowchart and process diagram for the DE stimulation program.
Figure 7:
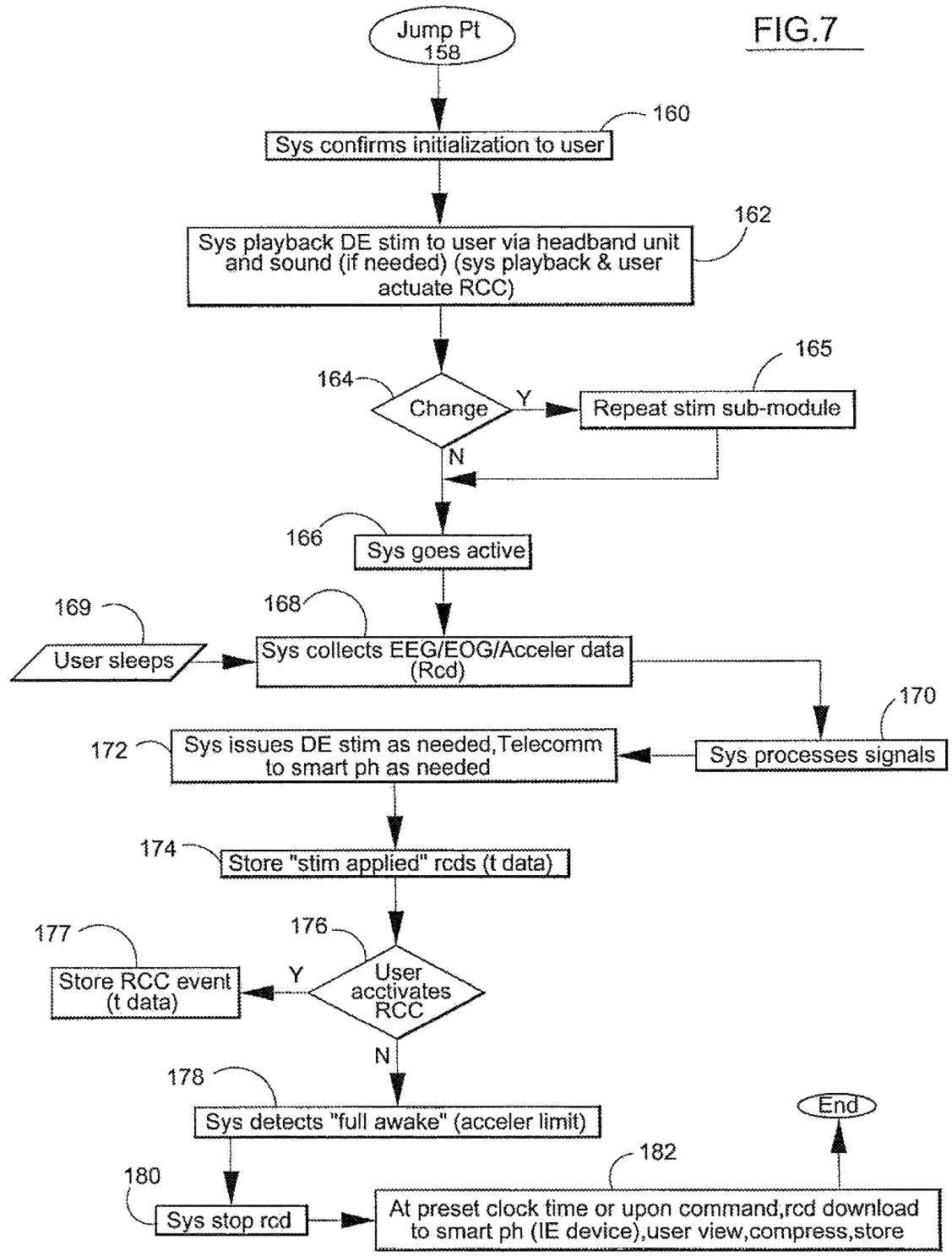
FIG. 7 diagrammatically illustrates a continuation of the DE stim program.

FIGS. 6 and 7 diagrammatically illustrate flowchart for the DE stim program 122. In step 124, the user selects "lucid dream" stimuli. The system selects either the fine detector or the coarse time detectors for detection of the REM and EEG/EOG signals. In step 126, the user selects "deep sleep" and the system selects either the fine time detector or coarse time detectors for sleep stage N3.

In path 127, the system branches to the clock-based or temporal limit program. In step 129, the user selects the DE stim ON clock time. In other words, the user would select a clock time which the system becomes active (ON) to detect REM signals and lucid dream events. When OFF, no DE stim is applied when REM is detected. The return path 131 passes through auto path 125.

Auto path 125 shows the ordinary DE stim selection sub-module 130. In other words, the user selects a "light" stimuli in block 132, a "sound" stimuli in block 134, or a "AV" combination stimuli (both light and sound) in block

136. The user selects these by having the smart phone display on display 76 the various colored lights and the various intensities. Selection is noted by the user's smart phone responses and the program selection 138. As for sounds, various sounds bites can be label displayed on display 76 and audibly presented on speaker 78 to the user. The sound bites are stored in memory 72. User makes a selection in selection box 140. The same selection for AV is made in program step 142.

After the user inputs his or her choices regarding the lucid stimuli commands (DE stim), the light commands and the audible commands and the AV commands, the system activates a decision block 144 which determines whether the coarse filter or coarse time detector should be activated. If not, the system activates the DE stimulation program for the fine feature detector as module 145. If the coarse time detector is activated from decision block 144, the YES branch is taken and the lucid stimuli command from user inputs 132, 134 or 136 are linked to the sleep stages detected by the coarse feature detector. In the illustrated embodiment, the REM coarse feature is detected. Other sleep stages may be subject to DE stim. After the lucid stimuli commands are stored in memory 41 of headband unit 30, the system determines whether both the fine time and the coarse time feature (F-C combo) detector is activated in decision step 148. If YES, the system loops back prior to coarse time feature extraction 144. Thereafter, the NO branch is taken from decision 144 and the fine feature extraction module 145 is activated. If not, the system in function block 150 plays back the stimuli from smart phone 32 with respect to audio from speaker 79 as well as plays back the light stimuli on the headband unit 30 by illuminating, in one embodiment, LEDs 60, 62.

In decision block 152, the system determines whether the user has selected reality check control ON. If not, the system executes step 153 which initializes the headband unit 30. The system then jumps to jump point 158 to FIG. 7. If the user has selected the RCC module, in step 154, the system sets the RCC module ON. In step 156, the user repeats the DE stim selection sub-module 130 and selects light, sound or AV combination for the RCC as well as intensity and color stim and sound elements. The system returns to "initialize head unit" and function block 153 and the system progresses to jump point 158 to FIG. 7.

FIG. 7, in step 160, confirms that the system has been initialized. This may involve either an audio visual presentation of confirmation or another playback routine. In step 162, the system plays back the DE stim to the user via the headband unit and the sound, if needed. The system playback also forces the user actuate the RCC control. This trains the user for the RCC function. In the manner, the user would be taught how to activate the RCC control and also know the RCC stimuli. The user, by activating the RCC stimuli, begins to train his brain to recognize the RCC stimuli when he or she is asleep. If the user actuates the RCC stimuli in a light sleep or REM stage, the user may recognize the RCC stimuli as part of the dream. If the user in a dream state notes conditions that represent the RCC stimuli but then, upon review of the EEG and time-based markers for RCC, discovers that the RCC circuit was not activated in the previous designated sleep cycle, the user notes that the system DE stimuli has triggered the lucid dream rather then the user activating the RCC stim.

Decision block 164 determines whether the user wants to change the DE stimuli. If yes, the system repeats stimuli sub-model module 130 in step 165. If NO, the system executes step 166 which activates the entire dream enhancement system. In step 168, the system collects EEG and EOG signals as well as accelerometer signals. This occurs when the user sleeps. See block 169. In step 170, the system processes the EEG, EOG and accelerometer data. Artifacts are removed and the signal REM and NREM waveforms are detected. In step 172, the system issues DE stimuli as needed pursuant to the user-supplied lucid stimuli commands. The "lucid dream stimuli" commands may be operable with NREM waveforms. As discussed later, an initial set preprogrammed DE stim may be used in the system. In step 172, the system issues the DE stimuli, turns ON the lights and activates the onboard telecommunications module 68 and the audio device or smart phone telecommunications module 169 to activate audio speaker 179 for the audio stimulus. Step 174 stores a "stimulus supplied" record as a time-based signal in either the transient memory 46 or the waveform memory 44.

Decision step 176 determines whether the user has activated the reality check RCC control. This RCC control in FIG. 3 is switch 51. Other input units can be utilized. If YES, the system executes in step 177, a store RCC actuated and other RCC events. This is a time-based marker. Also, the system would activate the RCC stimuli as pre-programmed by the user. From decision block 176, if the user has not activated the RCC command control, the system executes step 178 wherein the system detects a "full awake" condition of the user. This may be detected by an exceed limit threshold from the accelerometer. In step 180, the system stops recording the EEG and EOG. Also, there may be another "stop program" event when the signals from the EEG and EOG are absent or blocked (not processed) for a predetermined period of time. In step 182, the system at the preset clock time or upon command, sends a record upload to the smart phone or other internet enabled device. The user can view the EEG and EOG signal, the time-based markers, and the compressed and stored signal on other electronic devices such as the computers, laptops and IE device computer shown in FIG. 1. The process then ends.

Figure 8:
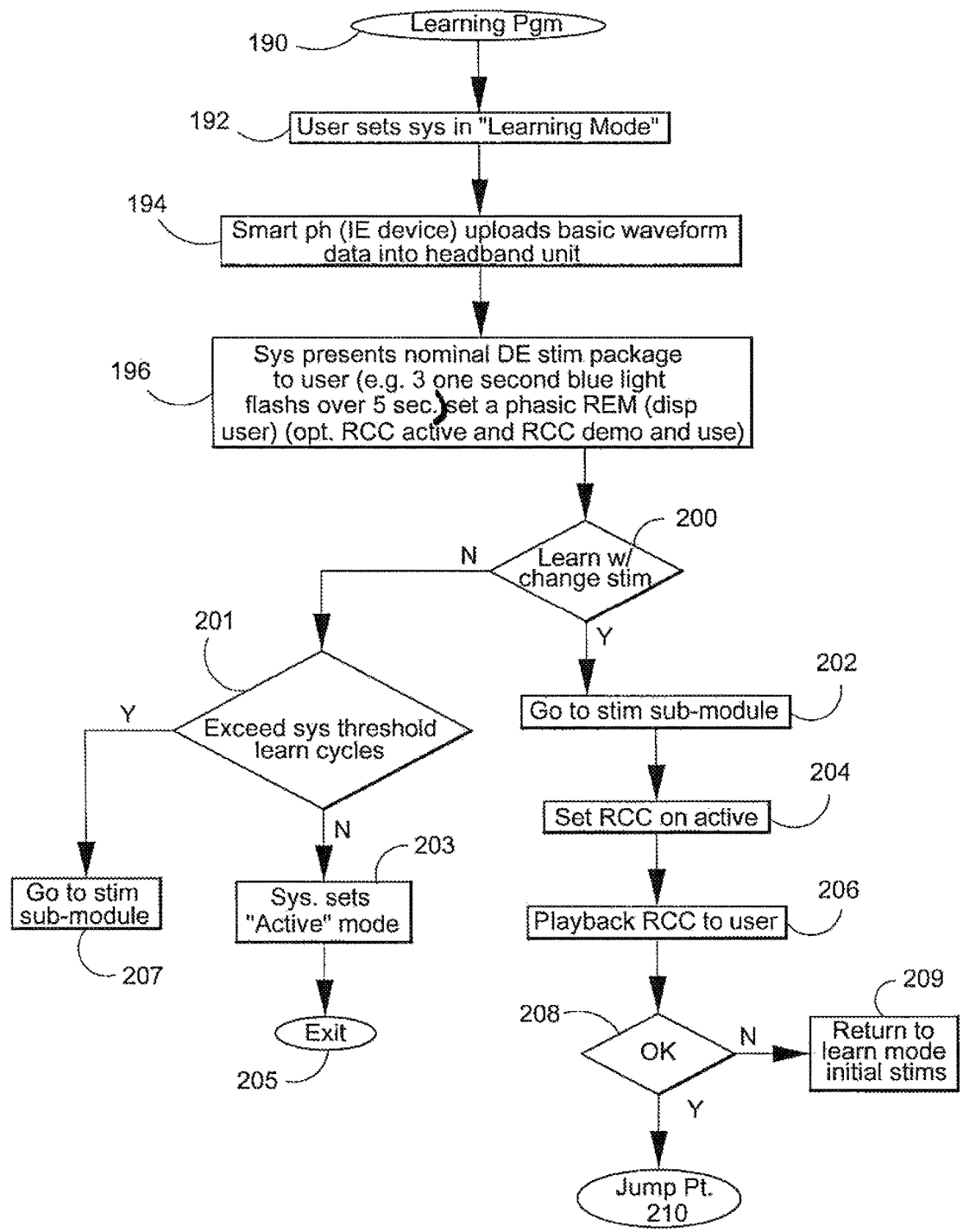
FIG. 8 diagrammatically illustrates a flowchart and process for the learning program.

FIG. 8 diagrammatically illustrates a flowchart for learning program 190. In step 192, the user sets ON the "learning mode." This may be a user selection from display 76 in smart phone 32. In step 194, the smart phone or internet enabled device uploads basic waveform baseline data and an initial DE stim set into the headband unit 32. This basic waveform data is a compilation of test subject data such that the headband is pre-programmed to detect certain EEG and EOG waveforms. This may avoid the "12 sleep cycle" training for the neural network. In step 196, the system presents a nominal DE stimulation package to the user. This nominal DE stimulation package may be displayed on display 76 of smart phone 32 and speaker 79 may play audio versions of audio DE stim. As an example in FIG. 8, the stimulus or the nominal or initial stimulus may be 3, one second blue light flashes presented to the user's eyes over a 5 second time window. The nominal DE stim package may be triggered by detection of a phasic REM. Optionally, the user may activate the reality check RCC control and the system demonstrates an initial RCC stimulus and RCC use. In decision step 200, a determination is made whether the learning program is to be changed by the user or not. If YES, the system executes, in step 202, a return to the DE stim sub-module 130. As explained above, the user selects light, sound or AV as part of the lucid dream stimulation. In step 204, the system sets, with the user approval, the RCC control ON or active. In step 206, the system plays back the RCC stimuli to the user. Decision 202 requires the user to accept or reject the learning stimuli set. If not, the system in step 209 returns to the learning mode initial steps. Those initial steps are basically steps prior to function module 196. If YES, the system jumps to jump point 210 of FIG. 9.

Returning back to decision step 200, if the learning program is not changed by the user, the NO branch is taken to decision step 201. Decision step 201 determines whether the learning program has exceeded a certain threshold or limit of "learned cycles." If YES, the system activates step 207 which returns the user to the stimuli selection submodule 130 of the DE stim program 122 in FIG. 6. If from decision step 201 the NO branch is taken, the system executes step 203 wherein the system sets the device to an active learning mode. The "learning active" state wherein the system uses the preset or initial set of DE stimuli in a learning condition. The system exits in step 205.

Figure 9:
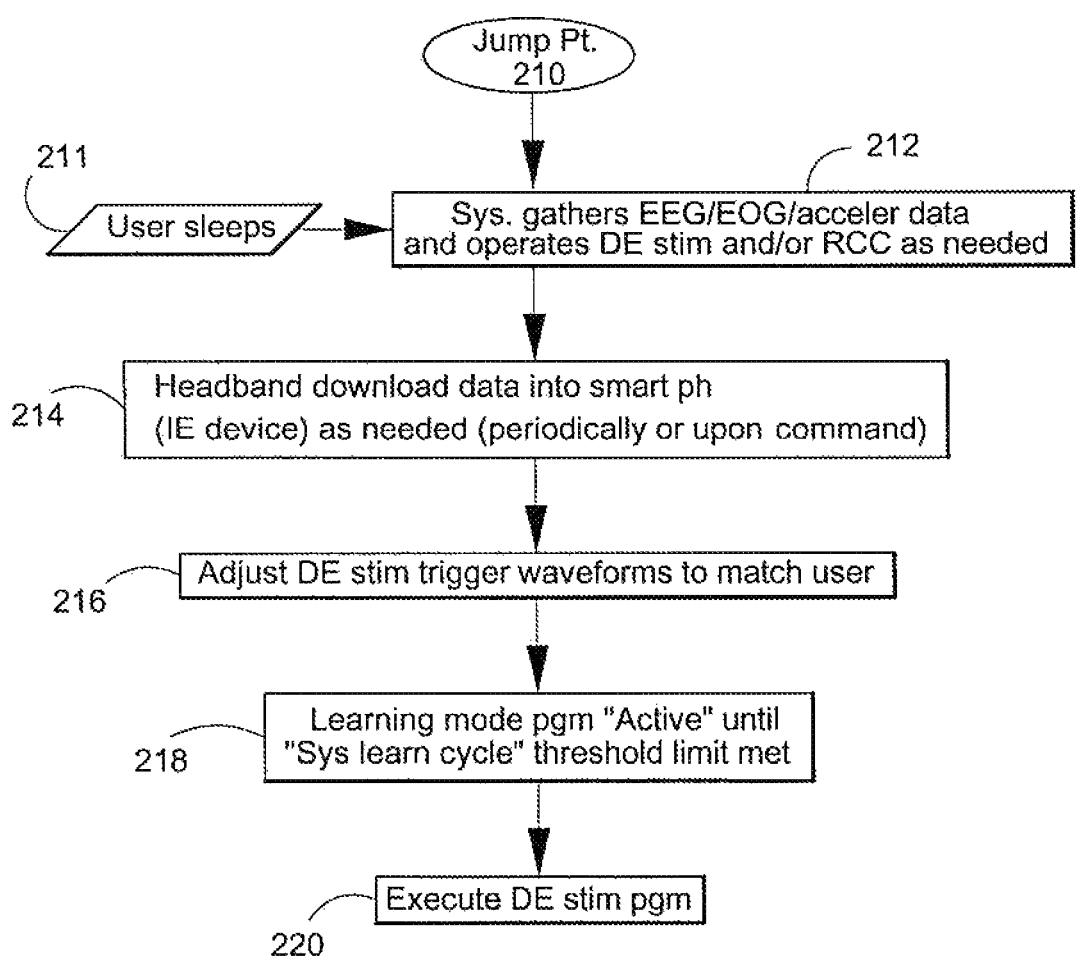
FIG. 9 diagrammatically illustrates a continuation of the learning program.

In FIG. 9, from jump point 210, the user "designated" sleep is noted in block 211. In block 212, the system gathers the EEG and EOG and accelerometer data for that user selected sleep cycle. The system operates and generates DE stim lucid command signals or RCC commands as needed. In function block 214, the headband unit uploads data into the smart phone or internet enabled devices needed. This may be periodically, such as in the morning after a long designated sleep period, or upon command. The command would be entered by the user on the smart phone 32 using touch activated display 76 or other keypad information commonly found in smart phones.

In step 216, the system adjusts the DE stimulus trigger waveform to match the user's waveforms. In other words, if the system has not detected a REM event during a designated sleep cycle, the initial waveform features may not be sensitive enough to the user's EEG and EOG signals. The algorithms for the waveform feature extraction may be altered until a REM event is detected. The system would go through many learning cycles and learning program adjustments for the waveform extraction features. The learning cycle count is monitored in step 201. In a similar manner, if REM transient signals are detected, and the system generates pre-programmed lucid stimuli commands, but if the user does not remain in the REM state, the system may alter the lucid stimuli commands or DE stim signals to, for example, increase the intensity of the light, change the color of the light, change the audio presentation (loudness, duration, type of sound) or may provide a combination of these changes. The system seeks to adjust trigger points to achieve multiple sequential REM waveforms, representing extended lucid dream stages. Further, the trigger point for issuing the DE stim may be time delayed from the detection of the REM transient. For example, the system may operate so fast that the DE stimuli is activated at a time wherein the user does not react. The DE stim may be too soon to keep the user in a REM sleep state. The REM transient or trigger signal for the DE stim may be delayed 2 or 3 seconds (or other time delay periods) such that the lucid stimuli is activated 3-4 seconds after the REM transient signal is identified by the feature detector. A similar analysis and change of either the feature extraction or the application of DE stim can be applied to the coarse time feature detector.

In step 218, the learning mode program which is active remains active until the system learning cycle has reached its threshold limit. As noted above, there is a limit to the number of times the learning cycle has altered DE stim to enhance lucid dream REM. Decision point 201 determines whether the learning threshold has been exceeded. In step 220, the system executes the DE stim program. In other words, once the REM cycle is detected and some lucid dream stimuli is activated to keep the user in a REM dream stage, the user is presented with the program to change the lucid stimuli commands and further enhance his or her dream state. If lucid REM stages are extended, the learning program may be turned off either automatically or by cycle count maximum.

Figure 10:
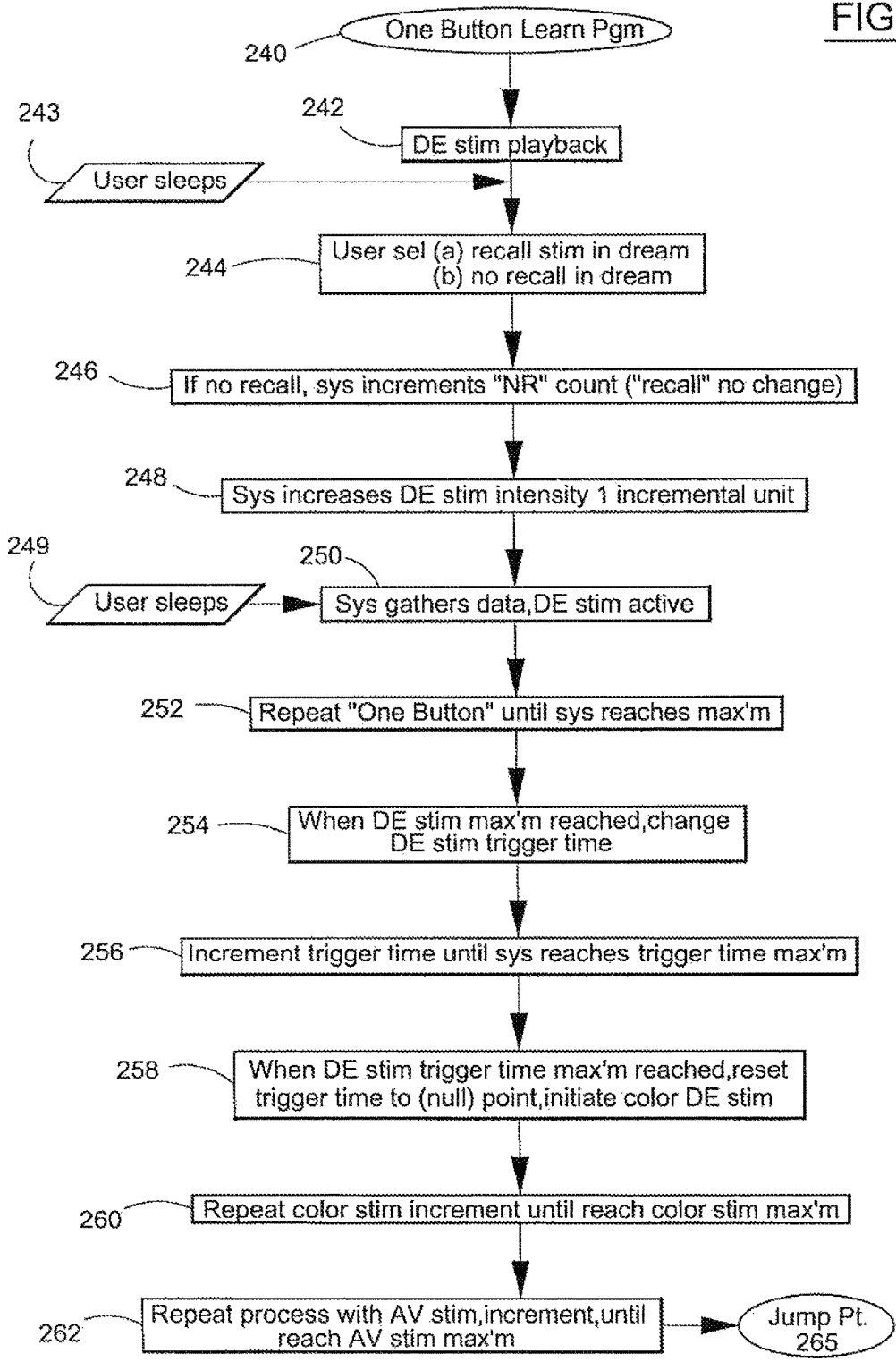
FIG. 10 diagrammatically illustrates a flowchart and process for a one button learn program.
Figure 11:
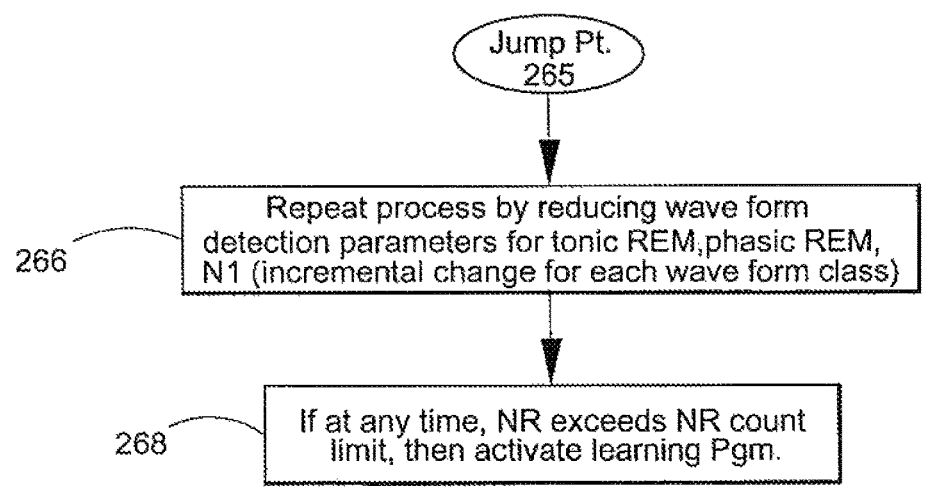
FIG. 11 diagrammatically illustrates a continuation of the learn program.

FIGS. 10 and 11 diagrammatically show a one button learn program 240. In step 242, the DE stim package is played back to the user. The DE stim package may be an initial DE stim or a user-supplied DE stim program package. In step 243, the user sleeps and the system attempts to provide REM stimulus and, in the subsequent step 244, the user selects, after the user awakes, a "recall" button or a "no recall" button (YES or NO on the smart phone). In other words, the user would sleep through the night wearing the headpiece unit. If the user recalls, after the user awakes, a lucid dream which matches the stimuli, the user in smart phone 32 selects the "recall" user interface. Otherwise, the user selects "no recall." If the user recalls a lucid dream and the stimulus in the user's dream, then the system is properly trained. If the user does not recall the stimuli generated by the headband unit, the "no recall" selection is made on touch screen display 76 in smart phone 32. In block 246, if the "no recall" condition is met, the system increments an NR (no recall) count. If the recall selection is made by the user, no change is made to the NR count unit. If the DE stim is a blue, medium intensity light pulse of one second flash, the system may increment to max intensity (or a 1.5 sec. flash at medium intensity). In step 248 under the "no recall" condition, the system increases the DE stim intensity one incremental unit. In step 250, the system gathers data as the user sleeps another night as noted in block 249. The system also applies the revised, incremented DE stim during that sleep cycle. In step 252, the system repeats the "one button learn" program until the DE stim reaches a maximum. The "repeat" refers to re-activation of steps 244 through 250, including the increment DE stim step 248, until the max threshold is reached. The max threshold for DE stim red light intensity may be 100% ON. Otherwise, a max time ON may be the stim max.

In step 254, when the DE stim maximum is reached, the system changes the DE trigger time. In other words, the system would increase the intensity of a selected light color until a maximum intensity is reached. At that point in time, the system in step 254 changes a trigger time or adds a delay time to the DE stim applied to the user after the REM transient is identified in the signal processing of onboard processor 36. Function block 256 increments the trigger delay time until the system reaches a maximum trigger delay time or threshold. In step 258, when the DE stim trigger time maximum is reached, the system will reset the trigger time to null point and initiate a color change for the DE stim. In step 260, the system repeats the color stim change increment until a color stim maximum is reached. In other words, the colors are changed until a "maximum" color is reached. The maximum color might be in the following sequence: blue, green, red. Red being the highest stimulus to be applied to the user. Of course, studies may show that different color combinations would result in greater stimuli to the user in a dream stage. Function block 262 repeats the process using audio and then audio visual stimuli, increases or increments the audio or the AV stimuli until an audio or AV maximum stimulus is reached. Different sound bites may be sequentially pre-programmed as incremental audio stim similar to the color stim increments. The system at jump point 265 transfers to FIG. 11.

In FIG. 11, function module 266 repeats the process by reducing or refining the waveform detection parameters for tonic REM, phasic REM and N1. This may include an incremental change for each waveform class. Changes may be made to the waveform detection algorithms.

In step 268, if at any time during the one button learning program, the NR count is exceeded, or reaches an NR count limit, then the system deactivates the learning program. In other words, the user when he or she selects the "one button learning program" should actively indicate after each major sleep cycle whether he or she recalls the lucid stimuli during the dream. If over a series of days, or weeks, and after each night the user selects no recall, the learning program would go ON thereby changing the stimulus, the intensity of stimulus, the type of stimulus, and the combinatory stimulus or AV stimulus. Of course, the order of this process may be changed, other than that disclosed in FIGS. 10 and 11. In other words, waveform change detection may be first and the color intensity of the DE stim may be second followed by the color change routine. Alternatively, the color change may be first and the waveform change may be last as shown in FIG. 11.

The learning program in FIG. 9 could also change a "flashing frequency" of the lights or the volume, intensity, combinatory aspects, type of sound, etc.

Figure 12:
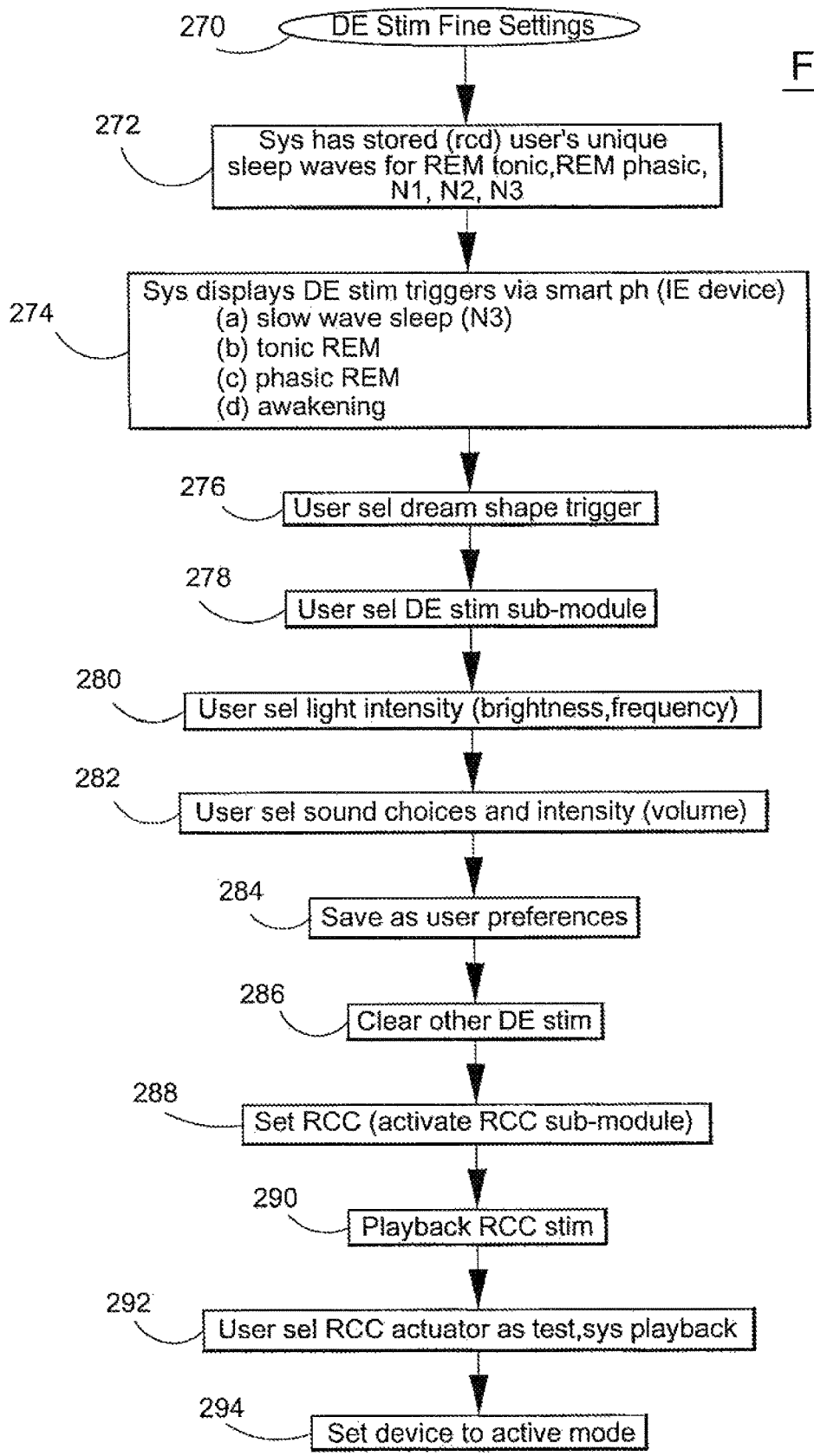
FIGS. 12 and 13 diagrammatically illustrates a DE stim fine time setting program as a flowchart and a process method.

FIG. 12 shows how the user sets the DE stim fine time settings in program 270. In step 272, the system has stored and recorded the user's unique sleep waves for REM tonic, REM phasic and N1, N2 and N3 (the 12 night normalization sequence to obtain the baseline waveform). In step 274, the system displays a user list of the DE stim triggers via the smart phone or internet enabled device. These DE stim triggers displayed for selection by the user are slow wave sleep (N3), tonic REM, phasic REM and awakening. In step 276, the user selects a particular dream stage trigger to be the subject of a user-programmed DE stim. In step 278, the user selects the DE stim sub-module. The input DE stim then becomes a DE stim command for the selected slow wave sleep, tonic REM, phasic REM or awakening trigger. The DE stim sub-module is shown in FIG. 6 as sub-module 130.

Figure 13:
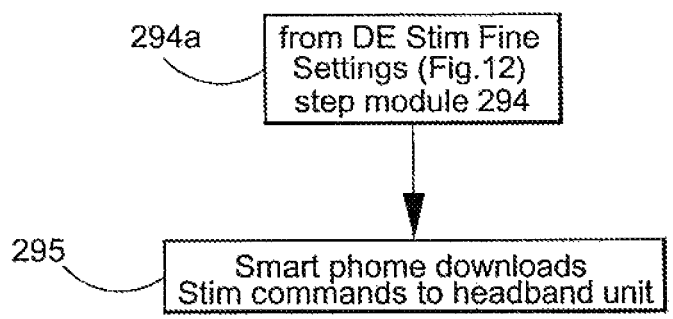

In step 280, the user selects for the DE stim the light and the light intensity, brightness, and frequency, if a flashing light is selected. In step 282, the user selects the sound choices and the intensity or volume of the sound. These sound choices are stored in memory 72 which is the audio playback memory of smart phone 32. In step 284, the system saves all these DE stim commands as user preferences. In step 286, the system clears other DE stimulus or lucid stimuli commands. In step 288, the system sets or activates the RCC sub-module for reality check control. In step 290 the system plays back the RCC stimulus. In step 292, the user selects the RCC actuator as a test and the system plays back the stim. In step 294, the system sets the headband device to "active mode." FIG. 13 shows continuation step 294*a* from FIG. 12. In step 295, the stim commands are then downloaded to the headband unit.

Figure 14:
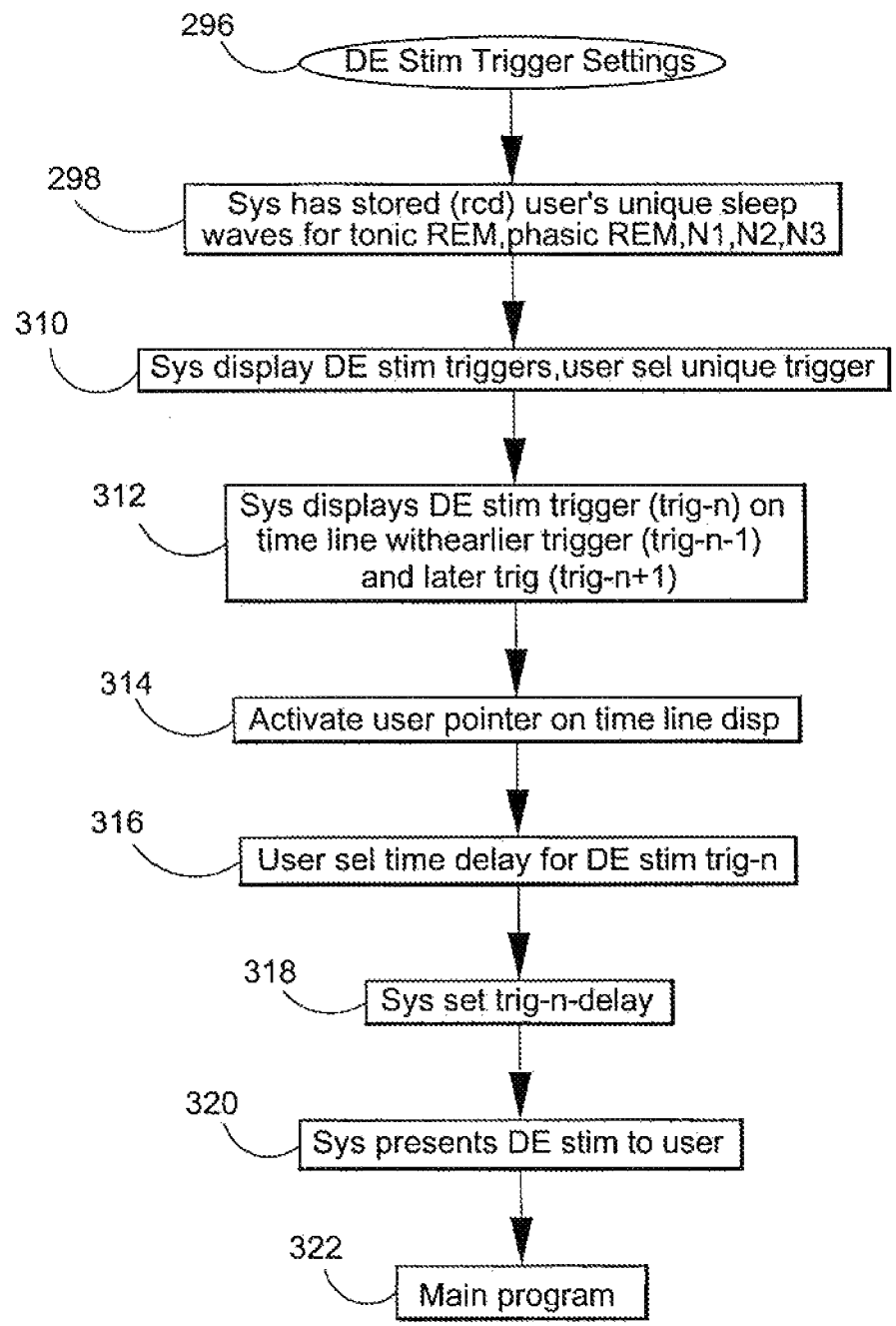
FIG. 14 diagrammatically illustrates a DE stim trigger setting program as a flowchart and a process.

FIG. 14 shows DE stimulus time trigger settings program 296. In step 298, the system has stored or recorded the user's unique sleep waves for tonic REM, phasic REM, N1, N2 and N3. In step 310, the system displays the DE stim time-based triggers and the user selects the unique dream stage trigger to be subject to the trigger time change. In step 312, the system displays the DE stim trigger on a time line on the smart phone 32 display 76. The time line is the EEG wave with the current DE stim trigger n shown as a line on the waveform timeline. The system may also suggest an earlier trigger point (which would trigger the DE stim lucid stimuli commands) that being a trigger set time n−1, or a later time trigger at time n+1. In step 314, the user activates a pointer on the time line display with the waveform and moves the proposed trigger point to n−1 or n+1. In step 316, the user selects a time delay (n−1 or n−2) for the DE stimulation trigger. That time delay is set, in step 318 as trigger n-delay signal. In step 320, the system presents the DE stim to the user and in step 322 the main program is activated. The DE stim trigger delay is downloaded to the head unit.

Regarding the user's ability to review the recorded EEG-EOG signal train and the REM indicators and DE stim indicators, the smart phone may audibly present the data rather than visually present the data to the user. Accordingly, the user would select a "audible playback" command to the smart phone. The phone would gather the records and audibly announce the REM markers and the associated time, and the DE stim markers and the time, and any other indicators, such as the RCC markers. A time based audio presentation is therefore presented to the user.

Figure 15:
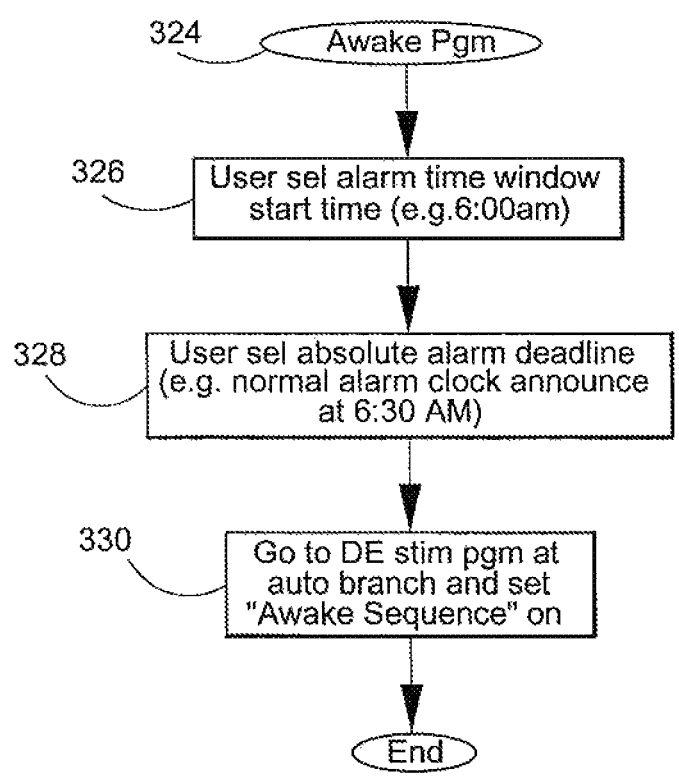
FIG. 15 diagrammatically illustrates an awake program as a flowchart and a process method.

FIG. 15 shows the awake program 324. In step 326, the user selects the alarm time window and a start time for the alarm time window. For example, the user may want to be awaken between 6 am and 6:30. In step 328, the user selects an absolute alarm deadline. In other words, the user may select a condition where the alarm absolutely is activated ON and an alarm signal is audibly presented to the user at 6:30 am. In step 330, the system permits the user to activate the DE stim program and particularly the auto branch and set the "awake sequence" ON. Therefore, during the awake program ON period, the system would sense REM signals from 6 am to 6:30. If a REM signal is detected within that 30 minute time cycle, the system would activate DE stim in accordance with user programmed items. If no REM was detected during that time frame, the system would issue a standard alarm clock audio alarm at 6:30.

Figure 16:
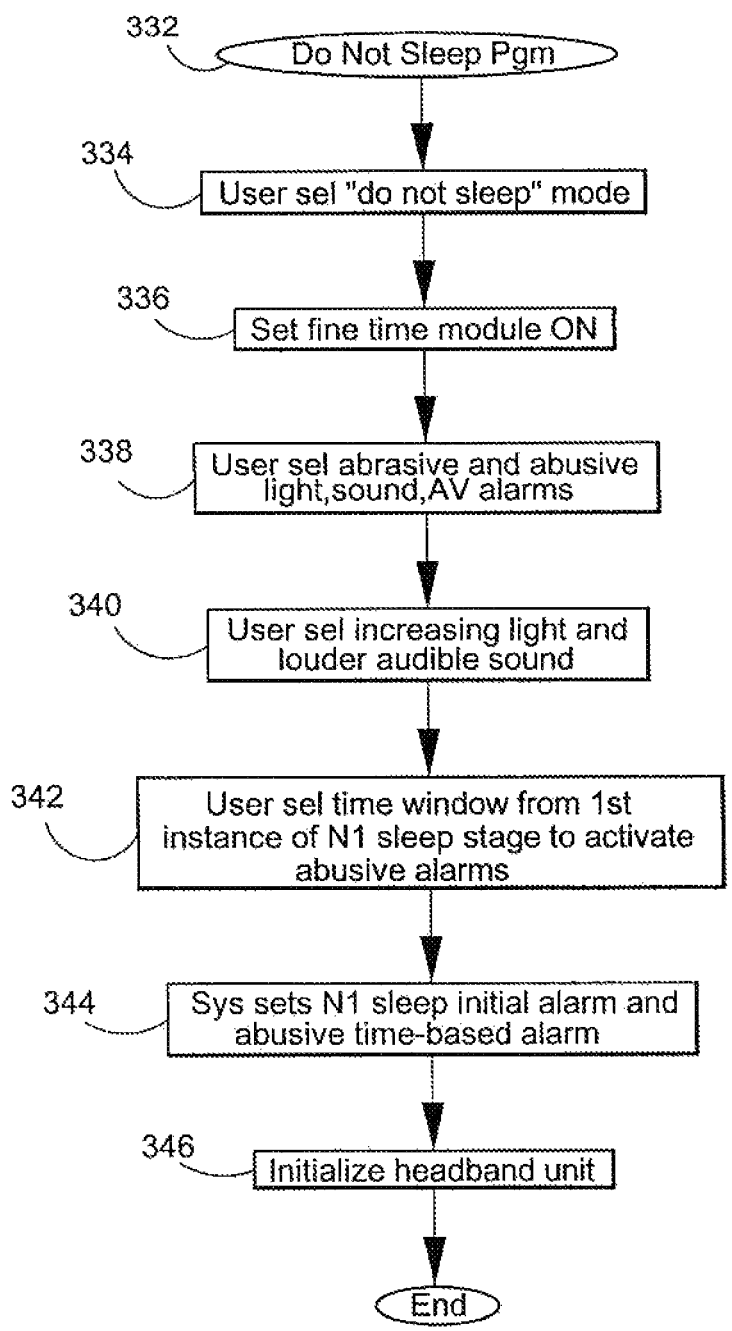
FIG. 16 diagrammatically illustrates a do not sleep program as a flowchart and a block process.

FIG. 16 shows the "do not sleep" program 332. In function block 334 the user selects "do not sleep" mode. This mode is selected by smart phone 32 and stored into a memory 72 and uploaded to the headband unit 30 and particularly processor 36 and memory 41. In step 336, the user sets the fine time feature extraction detector ON. In step 338, the user sets an abrasive and abusive light, sound and AV alarms. In step 340, the user selects increasing light and louder audible alarms depending upon the reoccurrence of the N1 light sleep detected EEG waveforms. In step 342, the user selects a time window from the first instance or first transient sense of N1 sleep stage to activate the abusive alarms. In other words, the user can select a delay from the detection of the transient N1 waveform. In step 344, the system sets the initial number of alarms and abusive time-based alarms. In step 346, the headband unit 30 is initialized.

In the drawings, and sometimes in the specification, reference is made to certain abbreviations. The following Abbreviations Table provides a correspondence between the abbreviations and the item or feature.

ABBREVIATIONS TABLE

| | |
|---|---|
| acceler | accelerometer |
| Admin | Administrator |
| alt. | alternate or optional path or step |
| ANN | artificial neural network, sometimes an AI network, artificial intelligence network or algorithm |
| API | application program interface |
| ASP | application service provider - server on a network |
| AV | audio visual, as in light and sound DE stimulus |
| bd | board |
| CD-RW | compact disk drive with read/write feature for CD disk |
| comm. | communications, typically telecommunications |
| comp | computer having internet enabled communications module |

ABBREVIATIONS TABLE-continued

| | |
|---|---|
| CPU | central processing unit |
| DB | data base |
| DE | dream enhancement, as in dream enhancement unit |
| DE stim | dream enhancement stimulation |
| Displ | display, typically display a web page or display certain information |
| doc | document |
| drv | drive, e.g., computer hard drive |
| DS | data storage |
| e | encryption |
| EEG | brainwave activity, typically electroencephalography |
| e.g. | for example |
| EOG | eye movement activity, typically electrooculography |
| em | email |
| equip | equipment |
| Geo | geographic location or code (geo.loc. is GPS data) |
| GPS | geo positioning system and location (optionally time data) |
| h-link | hyper link to a certain webpage or landing page |
| I/O | input/output |
| id | identify |
| ie or IE | Internet-enabled device, like a smartphone, tablet computer, computer, etc. |
| IP addr. | internet protocol address of internet enabled device |
| loc | location |
| mem | memory, including RAM, ROM, EPROM, flash, wave form memory (wave mem), transient memory (tran mem), waveform with "artifacts removed" memory (art rem mem) |
| Mess | message as in SMS or text message |
| mic | microphone or audio pickup device |
| ntwk | network, namely a telecomm network, typically internet based network. A local area network is also possible. |
| obj | object, for example, a data object |
| opt | optional or alternative program or module |
| pgm | program |
| ph | phone, namely an internet enabled phone, such as a smart phone |
| proc | processor, typically a microprocessor |
| pt. | point, as in jump point to another portion of the program |
| P/W | password |
| pwm | pulse width modulated signal or signal processor |
| pwr | power |
| Rcd | database record or record profile |
| re | regarding or relating to |
| RQT | request |
| rev | review |
| Rpt | Report |
| rt | real time, may include day and time stamp data |
| sch | search |
| sec | security |
| sel | select |
| sig cond | signal conditioner |
| smart ph | smart phone coupled to the internet |
| sms | text message |
| spkr | speaker or audio announcement device |
| stim | stimulus, as in DE stimulus |
| Svr | sever, as in web server |
| sys | system |
| Sys Op | System Operator |
| t | time |
| telecom | telecommunications system or network |
| tbl | tablet computer |
| trig | trigger as in DE stimulation trigger point |
| txr | transmitter - receiver device, maybe BLUETOOTH (tm), lan, wireless telecom network, or radio frequency |
| UPP | user's personal profile, for example an HC worker completes a UPP prior to inputting data about his or her HC application. |
| URL | Uniform Resource Locator, x pointer, or other network locator |
| w/ | with |
| w/in | within |
| w/out | without |
| wrt | with respect to |

Description of Typical System Features

The system described above notes that the user has a smartphone which has a telecomm link to the headband unit. Although a BLUETOOTH™ telecomm link is discussed, any type of telecomm network and i/o may be used. Further, the headband unit may have an onboard Internet-enabled (IE) device which is coupled to a wireless router or smart phone, cell phone with an ap (an access point), tablet computer, computer, or other IE device that is internet enabled. Computer tablets and other electronic devices may be configured in this manner.

The ap (an access point) or internet portal on the smartphone permits the person to access the onboard headband unit and system. If the user communicates with the system in a voice mode, the user interacts primarily with an interactive voice response system or module, an IVR.

The present invention relates processes data via computer systems, over the Internet and/or on a computer network (LAN or WAN), and computer programs, computer modules and information processing systems accomplish these signal processing services.

It is important to know that the embodiments illustrated herein and described herein below are only examples of the many advantageous uses of the innovative teachings set forth herein. In general, statements made in the specification of the present application do not necessarily limit any of the various claimed inventions. Moreover, some statements may apply to some inventive features but not to others. In general, unless otherwise indicated, singular elements may be in the plural and vice versa with no loss of generality. In the drawings, like numerals refer to like parts or features throughout the several views.

The present invention could be produced in hardware or software, or in a combination of hardware and software, and these implementations would be known to one of ordinary skill in the art. The system, or method, according to the inventive principles as disclosed in connection with the preferred embodiment, may be produced in a single computer system having separate elements or means for performing the individual functions or steps described or claimed or one or more elements or means combining the performance of any of the functions or steps disclosed or claimed, or may be arranged in a distributed computer system, interconnected by any suitable means as would be known by one of ordinary skill in the art.

According to the inventive principles as disclosed in connection with the preferred embodiments, the invention and the inventive principles are not limited to any particular kind of computer system but may be used with any general purpose computer, as would be known to one of ordinary skill in the art, arranged to perform the functions described and the method steps described. The operations of such a computer, as described above, may be according to a computer program contained on a medium for use in the operation or control of the computer as would be known to one of ordinary skill in the art. The computer medium which may be used to hold or contain the computer program product, may be a fixture of the computer such as an embedded memory or may be on a transportable medium such as a disk, as would be known to one of ordinary skill in the art. Further, the program, or components or modules thereof, may be downloaded from the Internet of otherwise through a computer network.

The invention is not limited to any particular computer program or logic or language, or instruction but may be practiced with any such suitable program, logic or language, or instructions as would be known to one of ordinary skill in the art. Without limiting the principles of the disclosed invention any such computing system can include, inter alia, at least a computer readable medium allowing a computer to read data, instructions, messages or message packets, and other computer readable information from the computer readable medium. The computer readable medium may include non-volatile memory, such as ROM, flash memory, floppy disk, disk drive memory, CD-ROM, and other permanent storage. Additionally, a computer readable medium may include, for example, volatile storage such as RAM, buffers, cache memory, and network circuits.

Furthermore, the computer readable medium may include computer readable information in a transitory state medium such as a network link and/or a network interface, including a wired network or a wireless network, that allow a computer to read such computer readable information.

Those of skill in the art will appreciate that the various illustrative modules, components, engines, and method steps described in connection with the above described figures and the embodiments disclosed herein can often be implemented as electronic hardware, software, firmware or combinations of the foregoing. To clearly illustrate this interchangeability of hardware and software, various illustrative modules and method steps have been described above generally in terms of their functionality. Whether such functionality is implemented as hardware or software depends upon the particular application and design constraints imposed on the overall system. Skilled persons can implement the described functionality in varying ways for each particular application, but such implementation decisions should not be interpreted as causing a departure from the scope of the invention. In addition, the grouping of functions within a module or step is for ease of description. Specific functions can be moved from one module or step to another without departing from the invention.

Moreover, the various illustrative modules, components, engines, and method steps described in connection with the embodiments disclosed herein can be implemented or performed with hardware such as a general purpose processor, a digital signal processor ("DSP"), an application specific integrated circuit ("ASIC"), field programmable gate array ("FPGA") or other programmable logic device, discrete gate or transistor logic, discrete hardware components, or any combination thereof designed to perform the functions described herein. A general-purpose processor is hardware and can be a microprocessor, but in the alternative, the processor can be any hardware processor or controller, microcontroller. A processor can also be implemented as a combination of computing devices, for example, a combination of a DSP and a microprocessor, a plurality of microprocessors, one or more microprocessors in conjunction with a DSP core, or any other such configuration.

Additionally, the steps of a method or algorithm and the functionality of a component, engine, or module described in connection with the embodiments disclosed herein can be embodied directly in hardware, in software executed by a processor, or in a combination of the two. Software can reside in computer or controller accessible computer-readable storage media including RAM memory, flash memory, ROM memory, EPROM memory, EEPROM memory, registers, hard disk, a removable disk, a CD-ROM, or any other form of storage medium including a network storage medium. An exemplary storage medium can be coupled to the processor such the processor can read information from, and write information to, the storage medium. In the alternative, the storage medium can be integral to the processor. The processor and the storage medium can also reside in an ASIC.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent exemplary embodiments of the invention and are therefore representative of the subject matter which is broadly contemplated by the present invention. It is further understood that the scope of the present invention fully encompasses other embodiments and that the scope of the present invention is accordingly limited by nothing other than the appended claims.

The claims appended hereto are meant to cover modifications and changes within the scope and spirit of the present invention.

What is claimed is:

1. A method for confirming a user's lucid dream stage comprising:
    providing a headband unit with one or more electroencephalography (EEG) and electrooculography (EOG) sensors, said headband unit adapted to be worn on the skull of the user with the one or more EEG and EOG sensors in skin contact;
    providing said headband unit with at least a plurality of light emitting devices mounted thereon to stimulate and illuminate the user's ocular senses with a plurality of distinctly different colored lights;
    providing an audio device having a telecommunications link with said headband unit, said audio device not physically attached to said headband unit;
    obtaining said one or more EEG and EOG signals from the user during a plurality of user sleep periods;
    over a plurality of normalization sleep periods, each normalization sleep period separated by an extended user awake period, detecting and storing data representative of the user's one or more EEG and EOG waveform patterns corresponding to rapid-eye-movement (REM) sleep, non-rapid-eye-movement (NREM) sleep stage one (NREM1), NREM sleep stage two (NREM2), and NREM sleep stage three (NREM3) as baseline data;
    normalizing the baseline data to obtain normalized data representative of the user's one or more REM, NREM1, NREM2, and NREM3;
    prior to a designated sleep period, obtaining one or more lucid stimuli commands from the user, said lucid stimuli commands corresponding to one or more of: (a) a visual light stimuli, (b) an audible audio stimuli and (c) an audio-visual (AV) stimuli being a combination of both visual light and audible audio stimuli;
    said light stimuli being one or more of said plurality of colored lights;
    said audio stimuli being one or more of a plurality of audible sounds directed at the user;
    after obtaining the one or more lucid stimuli commands from the user and during said designated sleep period, detecting REM sleep stage based upon newly acquired one or more EEG and EOG signals and the normalized data and thereafter generating a REM indicator;
    in the presence of said REM indicator and based upon said lucid stimuli commands, presenting respective one or more light stimuli, audio stimuli and AV stimuli directed at said user corresponding to user's lucid stimuli commands obtained from the user, said light stimuli generated by said light emitting devices and said audio stimuli presented by the audio device via said user's lucid stimuli commands generated by said headband unit and sent over the telecommunications link to the audio device from the headband unit.

2. A method for confirming a user's lucid dream stage as claimed in claim 1 further including:
providing a headband transceiver in said headband unit and providing onboard power in said headband unit:
providing a reality check control in said headband unit, said headband unit further including a user interface to activate the reality check control;
obtaining a reality check (RC) stimuli command from said user, said RC stimuli command corresponding to RC stimuli being one or more of: (a) said light stimuli, (b) said audio stimuli, (c) said AV stimuli;
during said designated sleep period and upon user actuation of said reality check control, presenting said RC stimuli directed at said user corresponding to the RC stimuli commands.

3. A method for confirming a user's lucid dream stage as claimed in claim 1 including:
during said designated sleep period, detecting REM sleep stage over both a 30 second epoch and a second additional a predetermined time-based window, said predetermined window being less than 15 seconds;
generating a plurality of REM indicators during the detection of both said 30 second epoch and the predetermined window; and
in the presence of each REM indicator, presenting said one or more light stimuli, audio stimuli and AV stimuli directed at said user based upon said user's lucid stimuli commands.

4. A method for confirming a user's lucid dream stage as claimed in 1 wherein said designated sleep period is one designated sleep period of a plurality of designated sleep periods, the method including:
obtaining a learning mode command from the user and thereafter, in a learning mode:
providing a pre-set initial set of lucid stimuli commands with corresponding one or more of: (a) said light stimuli, (b) said audio stimuli and (c) said AV stimuli, and providing a pre-set initial normalized data, said initial set of lucid stimuli commands replacing any earlier user supplied lucid stimuli commands;
in said learning mode, applying the pre-set initial set of lucid stimuli commands and the pre-set initial normalized data for (i) generation of said REM indicator and (ii) presentation of the corresponding one or more of said light stimuli, audio stimuli and AV stimuli based upon said pre-set initial set of lucid stimuli commands;
on said headband unit, providing a user actuatable interface for generating a lucid dream recall indicator;
during said learning mode and in the presence of the recall indicator, replacing any earlier user supplied lucid stimuli commands with the then applied lucid stimuli commands;
during said learning mode and during a sub-plurality of designated sleep periods after said one designated sleep period and in the absence of the recall indicator, changing one or more of: (a) a color of the light stimuli, (b) an intensity of the light stimuli, (c) an application of a flashing light stimuli, (d) a frequency of the flashing light stimuli, (e) an application of the audio stimuli, (f) an intensity of the audio stimuli, and (g) a sensory impact of the AV stimuli; and
during the learning mode and during said sub-plurality of designated sleep periods and in the continued absence of the recall indicator, changing said one or more of the light stimuli, audio stimuli and AV stimuli until said recall indicator is present and when said recall indicator is present thereafter using a then applied lucid stimuli commands as said user supplied lucid stimuli commands; and
thereafter ending said learning mode.

5. A method for confirming a user's lucid dream stage as claimed in 4 including:
in the presence of the recall indicator, obtaining said one or more lucid stimuli commands from the user.

6. A method for confirming a user's lucid dream stage comprising:
providing a headband unit with one or more electroencephalography (EEG) and electrooculography (EOG) sensors, said headband unit adapted to be worn on the skull of the user with the one or more EEG and EOG sensors in skin contact;
providing said headband unit with at least a plurality of light emitting devices mounted thereon to stimulate and illuminate the user's ocular senses with a plurality of distinctly different colored lights;
providing an audio device having a telecommunications link with said headband unit, said audio device not physically attached to said headband unit;
obtaining the one or more EEG and EOG signals from the user during a plurality of user sleep periods;
over said plurality of sleep periods, each sleep period separated by an extended user awake period, detecting and storing data representative of the user's one or more EEG and EOG waveform patterns corresponding to rapid-eye-movement (REM) sleep, non-rapid-eye-movement (NREM) sleep stage one (NREM1), NREM sleep stage two (NREM2), and NREM sleep stage three (NREM3) as baseline data;
providing pre-programmed one or more lucid stimuli commands prior to a designated sleep period of said plurality of sleep periods, said pre-programmed lucid stimuli commands having one or more of: (a) a visual light stimuli, (b) an audible audio stimuli, and (c) an audio-visual (AV) stimuli being a combination of both said light stimuli and audio stimuli, said light stimuli being one or more of said plurality of colored lights, said audio stimuli being one or more of a plurality of audible sounds directed at the user;
providing a user actuatable reality check (RC) control on said headband unit which, upon actuation by said user, generates a RC stimuli command;
during said designated sleep period, detecting REM sleep stage based upon said one or more EEG and EOG signals and generating a REM indicator based upon said baseline data;
in the presence of both said REM indicator and the user actuated RC stimuli command, applying said pre-programmed one or more lucid stimuli commands and presenting the corresponding light stimuli, audio stimuli and AV stimuli directed at said user, wherein said corresponding light stimuli being generated by said light emitting devices and wherein said audio stimuli being presented by said audio device via said pre-programmed lucid stimuli commands generated by said headband unit and sent over the telecommunications link to the audio device from the headband unit; and
subsequent to the presentation of said corresponding one or more of said light stimuli, audio stimuli and AV stimuli, using the last applied pre-programmed lucid stimuli commands as user-supplied lucid stimuli commands; and in a subsequent designated sleep period after said designated sleep period and in the presence of said REM indicator, applying said user-supplied lucid stimuli commands and presenting respective one or more of said light stimuli, audio stimuli and AV stimuli directed at said user.

7. A method for confirming a user's lucid dream stage as claimed in claim 6 wherein:

said user-supplied lucid stimuli commands is a first user-supplied lucid stimuli commands;

after said subsequent designated sleep period and before a following designated sleep period, said following designated sleep period being later than said subsequent designated sleep period, obtaining a second user-supplied lucid stimuli commands from the user, said second user-supplied lucid stimuli commands corresponding to one or more of said light stimuli, audio stimuli and AV stimuli; and, during said following designated sleep period and in the presence of said REM indicator, applying the second user-supplied lucid stimuli commands and presenting respective one or more of said light stimuli, audio stimuli and AV stimuli directed at said user.

8. A method for confirming a user's lucid dream stage comprising:

providing a headband unit with one or more electroencephalography (EEG) and electrooculography (EOG) sensors, said headband unit adapted to be worn on the skull of the user with the one or more EEG and EOG sensors in skin contact;

providing said headband unit with a processor coupled to a memory for storing and processing one or more lucid stimuli commands from said user, said processor and coupled memory further coupled to said one or more EEG or EOG sensors;

providing said headband unit with at least a plurality of light emitting devices mounted thereon to stimulate and illuminate the user's ocular senses with a plurality of distinctly different colored lights, said headband unit also having an audio device mounted thereon, said processor and coupled memory also coupled to said light emitting devices and said audio device;

obtaining the one or more EEG and EOG signals from the user during a plurality of user sleep periods;

over a plurality of normalization sleep periods, each normalization sleep period separated by an extended user awake period, detecting and storing data representative of the user's one or more EEG and EOG waveform patterns corresponding to rapid-eye-movement (REM) sleep, non-rapid-eye-movement (NREM) sleep stage one (NREM1), NREM sleep stage two (NREM2), and NREM sleep stage three (NREM3) as baseline data;

normalizing the baseline data to obtain normalized data representative of the user's REM, NREM1, NREM2, and NREM3;

prior to a designated sleep period which is either before or after said plurality of normalization sleep periods, obtaining one or more lucid stimuli commands from the user and storing the one or more lucid stimuli commands in said memory, said lucid stimuli commands corresponding to one or more of: (a) a visible light stimuli, (b) an audible audio stimuli, and (c) an audio-visual (AV) stimuli which is both a light stimuli and an audio stimuli, said light stimuli being one or more of said plurality of colored lights, said audio stimuli being one or more of a plurality of audible sounds directed at the user;

after obtaining said one or more lucid stimuli commands from the user and after said normalization sleep periods, detecting REM sleep stage based upon the one or more EEG and EOG signals obtained during the designated sleep period and the normalized data and thereafter generating a REM indicator;

in the presence of said REM indicator and based upon the one or more lucid stimuli commands, presenting the respective one or more light stimuli, audio stimuli and AV stimuli directed at said user corresponding to said one or more lucid stimuli commands, said respective one or more light stimuli, audio stimuli and AV stimuli generated by the headband unit.

\* \* \* \* \*